United States Patent
Kipps et al.

(10) Patent No.: US 11,548,953 B2
(45) Date of Patent: Jan. 10, 2023

(54) RECEPTOR TYROSINE KINASE-LIKE ORPHAN RECEPTOR 1 (ROR1) SINGLE CHAIN FV ANTIBODY FRAGMENT CONJUGATES AND METHODS OF USE THEREOF

(71) Applicant: THE REGENTS OF THE UNIVERSITY OF CALIFORNIA, Oakland, CA (US)

(72) Inventors: Thomas J. Kipps, San Diego, CA (US); Jianqianq Yu, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 132 days.

(21) Appl. No.: 17/093,474

(22) Filed: Nov. 9, 2020

(65) Prior Publication Data
US 2021/0171655 A1    Jun. 10, 2021

Related U.S. Application Data

(63) Continuation of application No. 15/908,659, filed on Feb. 28, 2018, now abandoned, which is a continuation of application No. 14/973,486, filed on Dec. 17, 2015, now Pat. No. 9,938,350, which is a continuation of application No. 13/703,864, filed as application No. PCT/US2011/040595 on Jun. 15, 2011, now Pat. No. 9,242,014.

(60) Provisional application No. 61/355,092, filed on Jun. 15, 2010.

(51) Int. Cl.
| | |
|---|---|
| C07K 16/30 | (2006.01) |
| C07K 14/725 | (2006.01) |
| C07K 16/40 | (2006.01) |
| C07K 16/46 | (2006.01) |
| C07K 14/705 | (2006.01) |
| G01N 33/574 | (2006.01) |

(52) U.S. Cl.
CPC .......... *C07K 16/30* (2013.01); *C07K 14/7051* (2013.01); *C07K 14/70521* (2013.01); *C07K 16/40* (2013.01); *C07K 16/46* (2013.01); *C07K 16/468* (2013.01); *G01N 33/57492* (2013.01); *C07K 2317/24* (2013.01); *C07K 2317/31* (2013.01); *C07K 2317/622* (2013.01); *C07K 2319/00* (2013.01); *C07K 2319/33* (2013.01); *G01N 2333/705* (2013.01)

(58) Field of Classification Search
CPC .... C07K 16/30; C07K 14/7051; C07K 16/40; C07K 2317/24; C07K 2317/31; C07K 2317/622; C07K 2319/00; C07K 2319/33
See application file for complete search history.

(56) References Cited

U.S. PATENT DOCUMENTS

| | | |
|---|---|---|
| 5,843,749 A | 12/1998 | Maisonpierre et al. |
| 6,586,251 B2 | 7/2003 | Economides et al. |
| 6,596,541 B2 | 7/2003 | Murphy et al. |
| 6,919,183 B2 | 7/2005 | Fandl et al. |
| 7,105,348 B2 | 9/2006 | Murphy et al. |
| 7,435,553 B2 | 10/2008 | Fandl et al. |
| 7,534,604 B2 | 5/2009 | Fandl et al. |
| 8,298,532 B2 | 10/2012 | Fandl et al. |
| 8,468,130 B2 | 6/2013 | Bhandari et al. |
| 8,470,324 B2 | 6/2013 | Fandl et al. |
| 8,597,898 B2 | 12/2013 | Fandl et al. |
| 8,710,022 B2 | 4/2014 | Takahashi et al. |
| 8,759,105 B2 | 6/2014 | Economides et al. |
| 8,846,402 B2 | 9/2014 | Economides et al. |
| 8,865,430 B2 | 10/2014 | Fandl et al. |
| 8,927,233 B2 | 1/2015 | Fandl et al. |
| 9,102,724 B2 | 8/2015 | Cummings et al. |
| 9,150,647 B2 | 10/2015 | Mellstedt et al. |
| 9,163,258 B2 | 10/2015 | Riddell et al. |
| 9,228,023 B2 | 1/2016 | Rohlff et al. |
| 9,228,208 B2 | 1/2016 | Frendewey et al. |
| 9,242,014 B2 | 1/2016 | Kipps et al. |
| 9,266,952 B2 | 2/2016 | Teige |
| 9,316,646 B2 | 4/2016 | Rader et al. |
| 9,938,350 B2 | 4/2018 | Kipps et al. |
| 2009/0137416 A1 | 5/2009 | Fandl et al. |
| 2010/0129817 A1 | 5/2010 | Wei et al. |
| 2011/0165650 A1 | 7/2011 | Fandl et al. |
| 2012/0282177 A1 | 11/2012 | Rohlff et al. |

(Continued)

FOREIGN PATENT DOCUMENTS

| | | |
|---|---|---|
| CN | 103792364 A | 5/2014 |
| EP | 2 617 320 A1 | 7/2013 |

(Continued)

OTHER PUBLICATIONS

Baskar, S. et al. (Jan. 15, 2008. "Unique cell surface expression of receptor tyrosine kinase ROR1 in human B-cell chronic lymphocytic leukemia," *Clin. Cancer Res.* 14(2):396-404.

(Continued)

*Primary Examiner* — Ruixiang Li
(74) *Attorney, Agent, or Firm* — Mintz, Levin, Cohn, Ferris, Glovsky and Popeo, P.C.

(57) ABSTRACT

Compositions including an antibody single-chain variable fragment (scFv) conjugate that specifically binds to ROR1 tumor-associated antigen are provided. The anti-ROR1 scFv antibody and conjugates may include a biologically-active molecule. Such conjugates may comprise a chimeric receptor to direct T cells to respond to ROR1 cancer cells, Methods to use the scFV conjugates to target cells expressing ROR1 for therapeutic and diagnostic purposes are also provided.

10 Claims, 12 Drawing Sheets

Specification includes a Sequence Listing.

(56) References Cited

U.S. PATENT DOCUMENTS

| | | |
|---|---|---|
| 2014/0072979 A1 | 3/2014 | Fandl et al. |
| 2014/0072980 A1 | 3/2014 | Fandl et al. |
| 2014/0134719 A1 | 5/2014 | Despande et al. |
| 2018/0362657 A1 | 12/2018 | Kipps et al. |

FOREIGN PATENT DOCUMENTS

| | | |
|---|---|---|
| WO | WO-2007/146957 A2 | 12/2007 |
| WO | WO-2007/146957 A3 | 12/2007 |
| WO | WO-2008/076868 A2 | 6/2008 |
| WO | WO-2008/076868 A3 | 6/2008 |
| WO | WO-2008/103849 A2 | 8/2008 |
| WO | WO-2008/103849 A3 | 8/2008 |
| WO | WO-2010/008069 A1 | 1/2010 |
| WO | WO-2010/124188 A1 | 10/2010 |
| WO | WO-2011/054007 A1 | 5/2011 |
| WO | WO-2011/079902 A2 | 7/2011 |
| WO | WO-2011/079902 A3 | 7/2011 |
| WO | WO-2011/159847 A2 | 12/2011 |
| WO | WO-2011/159847 A3 | 12/2011 |
| WO | WO-2012/076066 A1 | 6/2012 |
| WO | WO-2012/076727 A1 | 6/2012 |
| WO | WO-2014/167022 A1 | 10/2014 |

OTHER PUBLICATIONS

Brown, M. et al. (May 1, 1996). "Tolerance of single, but not multiple, amino acid replacements in antibody VH CDR 2: a means of minimizing B cell wastage from somatic hypermutation?," *J. Immunology* 156(9):3285-3291.

Daneshmanesh, A.H. et al. (Sep. 1, 2008). "ROR1, a Cell Surface Receptor Tyrosine Kinase is Expressed in Chronic Lymphocytic Leukemia and May Serve as a Putative Target for Therapy," *Int. J. Cancer*: 123(5):1190-1195.

Paul, W.E. (1993). Fundamental Immunology, 3rd Edition, Raven Press, New York, pp. 292-295.

Rudikoff, S. et al. (Mar. 1982). "Single amino acid substitution altering antigen-binding specificity," *Proc. Natl. Acad. Sci. USA* 79(6):1979-1983.

Vajdos, F.F. et al. (Jul. 5, 2002). Comprehensive functional maps of the antigen-binding site of an anti-ErbB2 antibody obtained with shotgun scanning mutagenesis, *J. Mol. Biol.* 320(2):415-428.

```
1
GAA TTC GGA TCC GCC ACC ATG GGA TGG TCA TGT ATC ATC CTT TTT CTA GTA
GCA ACT GCA ACC GGT GTA CAT TCC GAC ATC AAG ATG ACC CAG TCT CCA TCT
TCC ATG TAT GCA TCT CTA GGA GAG AGA GTC ACT ATC ACT TGC AAG GCG AGT
CCG GAC ATT AAT AGC TAT TTA AGC TGG TTC CAG CAG AAA CCA GGG AAA TCT
CCT AAG ACC CTG ATC TAT CGT GCA AAC AGA TTG GTT GAT GGG GTC CCA TCA
AGG TTC AGT GGC GGT GGA TCT GGG CAA GAT TAT TCT CTC ACC ATC AAC AGC
CTG GAG TAT GAA GAT ATG GGA ATT TAT TAT TGT CTA CAG TAT GAT GAA TTT
CCG TAC ACG TTC GGA GGG GGG ACC AAG CTG GAA ATG AAA GGC TCC ACC TCT
GGA TCC GGC AAG CCC GGA TCT GGC GAG GGA TCC ACC AAG GGC GAA GTG AAA
CTG GTG GAG TCT GGG GGA GGC TTA GTG AAG CCT GGA GGG TCC CTG AAA CTC
TCC TGT GCA GCC TCT GGA TTC ACT TTC AGT AGC TAT GCC ATG TCT TGG GTT
CGC CAG ATT CCA GAG AAG AGG CTG GAG TGG GTC GCA TCC ATT AGT CGT GGT
GGT ACC ACC TAC TAT CCA GAC AGT GTG AAG GGC CGA TTC ACC ATC TCC AGA
GAT AAT GTC AGG AAC ATC CTG TAC CTG CAA ATG AGC AGT CTG AGG TCT GAG
GAC ACG GCC ATG TAT TAC TGT GGA AGA TAT GAT TAC GAC GGG TAC TAT GCA
ATG GAC TAC TGG GGT CAA GGA ACC TCA GTC ACC GTC TCC TCA
                                                        807
```

Fig. 3

```
GAC ATC AAG ATG ACC CAG TCT CCA TCT TCC ATG TAT GCA TCT CTA GGA GAG
AGA GTC ACT ATC ACT TGC AAG GCG AGT CCG GAC ATT AAT AGC TAT TTA AGC
TGG TTC CAG CAG AAA CCA GGG AAA TCT CCT AAG ACC CTG ATC TAT CGT GCA
AAC AGA TTG GTT GAT GGG GTC CCA TCA AGG TTC AGT GGC GGT GGA TCT GGG
CAA GAT TAT TCT CTC ACC ATC AAC AGC CTG GAG TAT GAA GAT ATG GGA ATT
TAT TAT TGT CTA CAG TAT GAT GAA TTT CCG TAC ACG TTC GGA GGG GGG ACC
AAG CTG GAA ATG AAA GGC TCC ACC TCT GGA TCC GGC AAG CCC GGA TCT GGC
GAG GGA TCC ACC AAG GGC GAA GTG AAA CTG GTG GAG TCT GGG GGA GGC TTA
GTG AAG CCT GGA GGG TCC CTG AAA CTC TCC TGT GCA GCC TCT GGA TTC ACT
TTC AGT AGC TAT GCC ATG TCT TGG GTT CGC CAG ATT CCA GAG AAG AGG CTG
GAG TGG GTC GCA TCC ATT AGT CGT GGT GGT ACC ACC TAC TAT CCA GAC AGT
GTG AAG GGC CGA TTC ACC ATC TCC AGA GAT AAT GTC AGG AAC ATC CTG TAC
CTG CAA ATG AGC AGT CTG AGG TCT GAG GAC ACG GCC ATG TAT TAC TGT GGA
AGA TAT GAT TAC GAC GGG TAC TAT GCA ATG GAC TAC TGG GGT CAA GGA ACC
TCA GTC ACC GTC TCC TCA
```

Fig. 4

RECEPTOR TYROSINE KINASE-LIKE ORPHAN RECEPTOR 1 (ROR1) SINGLE CHAIN FV ANTIBODY FRAGMENT CONJUGATES AND METHODS OF USE THEREOF

CROSS-REFERENCES TO RELATED APPLICATIONS

This application is a continuation application of U.S. application Ser. No. 15/908,659, filed Feb. 28, 2018, which is a continuation of U.S. application Ser. No. 14/973,486, filed Dec. 17, 2015, which is a continuation of U.S. application Ser. No. 13/703,864, filed Dec. 12, 2012, which in turn is a U.S. National Stage of International Application No. PCT/US2011/040595, filed Jun. 15, 2011, which claims the benefit of U.S. Provisional Application No. 61/355,092, filed Jun. 15, 2010, each of which is incorporated herein by reference in its entirety and for all purposes.

STATEMENT AS TO RIGHTS TO INVENTIONS MADE UNDER FEDERALLY SPONSORED RESEARCH AND DEVELOPMENT

This invention was made with Government support under Grant Number P01 CA081534 from the National Institutes of Health. The Government may have certain rights in this invention.

REFERENCE TO A "SEQUENCE LISTING," A TABLE, OR A COMPUTER PROGRAM LISTING APPENDIX SUBMITTED AS AN ASCII FILE

The Sequence Listing written in file 048537-555C02US_ST25.TXT, created on Feb. 28, 2018, 8,879 bytes, machine format IBM-PC, MS-Windows operating system, is hereby incorporated by reference.

BACKGROUND OF THE INVENTION

Field of the Invention

The present invention relates generally to single chain Fv fragments of tumor-associated antigen binding antibodies. The invention further relates to single chain Fv conjugate molecules and their use in the delivery of biologically active molecules to cancer cells as well as in directing T cells to respond to tumor-associated antigen expressing cancer cells.

Background Information

Microarray analyses have revealed that there are genes expressed by CLL cells that are not expressed in other lymphoid tissues. Coupled with the observation that CLL cells also express a highly restricted immunoglobulin repertoire, cells likely express distinctive antigens that also could be targeted for immunotherapy. Conceivably, chronic lymphocytic leukemia (CLL) cells in particular also might have such leukemia-associated antigens (LAA).

However, CLL patients typically develop hypogammmaglobulinemia and worsening immune deficiency, which impairs their immune response to LAA-targeted vaccines. Implicated in the abnormal immune function are immune-suppressive factors and an acquired functional deficiency of CD154. Furthermore, CLL cells are particularly poor at antigen presentation, which appears in part secondary to inadequate leukemia-cell expression of immune co-stimulatory/adhesion molecules.

Indeed, despite the presence of tumor-associated antigens (TAAs) like LAAs expressed in different cancers, cancer patients typically are unable to mount an effective immune response against existing or developing tumors. TAA. binding antibodies have been used to develop potential cancer vaccines with mixed degrees of success. Many such TAAs represent developmental or differentiation antigens that have restricted expression. Fc containing antibodies to TAAs are often cleared relatively quickly from circulation and may be recognized only by one type of MHC molecule, limiting their usefulness in therapy.

Activation of CLL cells via CD40-ligation can reverse its immune-suppressive phenotype. Furthermore, CLL cells transduced with an adenovirus encoding the ligand for CD40 (Ad-CD154) can function as more effective antigen-presenting cells (APCs). In addition, they can effect ligation of CD40 on bystander leukemia B cells and stimulate autologous leukemia-reactive T cells both in vitro and in vivo. However, targeting of CD154 modified T cells to CLL cells remains to be achieved.

Tyrosine kinases are important mediators of the signaling cascade, determining key roles in diverse biological processes like growth, differentiation, metabolism and apoptosis in response to external and internal stimuli. Studies have implicated the role of tyrosine kinases in the pathophysiology of cancer. Schlessinger J. (2000) Cell, 103:211-225; and Robinson et al. (2000) Oncogene, 19:5548-5557. MacKeigan and colleagues used a large-scale RNAi approach to identify kinases that might regulate survival and apoptosis of a human tumor cell line (HeLa), RNAi to ROR1 was found as one of the most potent in inducing apoptosis among the set of RNAi targeting each of 73 different kinase-encoding genes. MacKeigan et al. (2005) Nat Cell Biol., 7:591-600. However, these investigators did not examine the expression or function of ROR1 protein in these cells.

ROR1 is a membrane-receptor with an intracellular kinase-like domain and extracellular Frizzled-like cysteine-rich domain, which is common to receptors of members of the Wnt-family. ROR1 is member of the ROR family that is evolutionarily conserved among *Caenorhavditis elegans*, *Drosophila*, mice and humans. Wilson C, Goberdhan D C, Steller H. Dror, a potential neurotrophic receptor gene, encodes a *Drosophila* homolog of the vertebrate: Ror family of Trk-related receptor tyrosine kinases. Proc Natl Acad Sci USA. 1993; 90:7109-7113; Oishi et al. (1997) J Biol. Chem., 272:11916-11923; Masiakowski et al. (1992) J Biol. Chem., 267:26181-26190; Forrester et al. (2002) Cell Mo! Life Sci., 59:83-96; and Oishi et al. (1999) Genes Cells, 4:41-56. In rodents, ROR1 is expressed primarily in developing cephalic neural crest in the dorsal part of the diencephalons and mid-hind brain boundary during embryogenesis. In most species examined, expression of ROR1 apparently attenuates during embryonic development, becoming negligible at term. ROR1 mRNA was reported to express in infant brain, renal cancer and colon cancer. In a recent study, it was found that ROR1, at both mRNA and protein level, was highly expressed in CLL B cells but not normal B cells. Moreover, it was found that ROR.1 is a receptor for Wnt5a, which could induce activation of NF-κB when co-expressed with RORI in HEK293 cells and enhance survival of CLL cells in vitro. Another study found that RORI was expressed in acute lymphocytic leukemia (ALL) as well. Shabani et al. (2007) Tumour Biol., 28:318-326; and Baskar et al. (2008) Clin Cancer Res., 14:396-404.

Expression of full-length RORI in numerous cancer cell lines and samples, but not other tissues, including blood or splenic lymphocytes of non-leukemic patients or normal adult donors, and also generated mouse anti-sera against full-length human RORI. Fukuda et al., Blood: ASH Annual Meeting Abstracts 2004 104, Abstract 772 (2004) (incorporated herein by reference in its entirety). The polypeptide and coding sequences for RORI have been reported elsewhere and are also incorporated herein by this reference (see, e.g., Accession Nos. NP 005003.2 and NM 005012). Surprisingly, it has also been discovered that cancer cells which express the Wnt5a protein, such as CLL cells, not only bind RORI but have a survival advantage conferred as a consequence.

Thus, ROR 1 is an embryonic protein that is expressed uniquely on certain cancer cells, including in CLL, small lymphocytic lymphoma, marginal cell B-Cell lymphoma, Burkett's Lymphoma, and other cancers (e.g., breast cancers), but not on normal adult tissues and cells. It is therefore a potential TAA target for modulation of an immune response to ROR1 expressing cancer cells ("ROR1 cancers").

Yet, as noted. patients with CLL typically develop disease-related hypogammaglobulinemia and respond poorly to vaccines. The progressive acquired immune deficiency associated with CLL accounts for much of the morbidity related to this disease. However, as shown previously, following treatment with autologous Ad-CD154-transduced CLL cells, most patients had increased serum IgM and IgG and developed a specific antibody response against adenovirus and some developed anti-CLL autoantibodies. Although virus infections occasionally can induce autoantibodies, autoantibodies were not detected against other blood cells or human CD154. Likewise, there were no increases in the titer of antibodies to a recall antigen, tentanus toxoid, except in one patient who was immunized with tetanus toxoid following the second infusion of autologous Ad-CD 154-CLL cells. Therefore, CLL patients could respond well against other vaccines administered during the course of such treatment, potentially allowing for generation of protective immunity against infectious agents that commonly afflict patients with this disease. The invention provides such a vaccine, as well as targeting means for drug delivery to ROR1 cancer cells.

SUMMARY OF THE INVENTION

The present invention is based on the seminal generation or an anti-ROR1 single-chain variable fragment (scFv) antibody, as well as conjugates thereof which include a biologically active molecule. Such conjugates may comprise a chimeric receptor to direct T cells to respond to ROR1 cancer cells. Thus, the scFv may be used to target cells expressing: ROR.1 for therapeutic and diagnostic purposes.

In one aspect, the present invention provides an antibody single-chain variable fragment (scFv) conjugate. The conjugate includes an scFv having an amino acid sequence at least 90% identical to SEQ ID NO: 1 or SEQ ID NO: 2, and a biologically active molecule. In various embodiments, the biologically active molecule is selected from the group consisting of a polypeptide, a peptidomimetic, a nucleic acid molecule, a lipid, a drug compound, chemotherapeutic agent, a liposome, an antagonist and an agonist.

In another aspect, the present invention provides an isolated peptide including an amino acid sequence at least 90% identical to SEQ ID NO: 1 or SEQ ID NO: 2.

In various embodiments, the conjugate and peptide include an amino acid sequence at least 95% identical to SEQ ID NO: 1 or SEQ ID NO: 2. In exemplary embodiments, the conjugate and peptide has a binding specificity of an antibody as produced by a hybridoma having Accession No. PTA 8634 by the American Type Culture Collection.

In another aspect, the present invention provides an isolated nucleic acid encoding the conjugate or peptide of the invention.

In another aspect, the present invention provides a pharmaceutical composition including the conjugate or peptide of the invention an optionally a pharmaceutically acceptable carrier.

In another aspect, the present invention provides a method of producing a scFv antibody conjugate. The method includes transforming a host cell with an expression construct including a nucleic acid molecule encoding a scFv antibody and a polypeptide, the scFv peptide including an amino acid sequence at least 90% identical to SEQ ID NO: 1 or SEQ ID NO: 2; and culturing the host cell under conditions suitable for producing the conjugate, thereby producing the protein conjugate.

In another aspect, the present invention provides a method for detecting ROR1 protein in a sample, utilizing a delectably labeled scFv of the invention.

In another aspect, the present invention provides a method of targeting a biologically active molecule to a cell having an ROR1 receptor. The method includes contacting the cell with an scFv conjugate of the invention.

In another aspect, the present invention provides a kit to detect the presence of ROR1 protein in a sample from a subject that is known or suspected to contain cancer cells. The kit includes the an scFv antibody conjugate or peptide of the invention and instructions for its use in an assay environment.

In another aspect, the present invention provides a method for treating a ROR1 cancer in a human subject using an scFv antibody conjugate or peptide of the invention.

In another aspect, the present invention provides a method for treating or preventing CLL in which ROR1 binding of Wnt5a on CLL cells confers a survival advantage thereon by administering an scFv antibody conjugate or peptide of the invention.

In another aspect, the present invention provides a method of monitoring a therapeutic regimen for treating a subject having or at risk of having an ROR1 cancer using an scFv antibody conjugate or peptide of the invention.

BRIEF DESCRIPTION OF THE DRAWINGS

FIG. 1 shows the amino acid sequence (SEQ ID NO: 1) of an anti-R OR1 mAb scFv. The amino acid sequence includes a leader sequence (amino acid residues 1 to 25) and VL (amino acid residues 25 to 132) and VH (amino acid residues 151 to 269) chains joined by a linker sequence (amino acid residues 133 to 150). Legend of sub-sequences of SEQ ID NO:1: PDINSY (SEQ ID NO:7); RAN (SEQ ID NO:8); LQYDEFPYT (SEQ ID NO:9); GFTFSSYA (SEQ ID NO:10); ISRGGTT (SEQ ID NO:11); YDYDGYYAMDY (SEQ ID NO:12).

FIG. 2 shows the amino acid sequence (SEQ ID NO: 2) of an anti-ROR1 mAb scFv after cleavage of the leader during processing of the polypeptide.

FIG. 3 shows the nucleotide sequence encoding the anti-ROR1 mAb scFv (SEQ ID NO: 3) of SEQ ID NO: 1.

FIG. 4 shows the nucleotide sequence encoding the anti-ROR1 mAb scFv (SEQ ID NO: 4) of SEQ ID NO: 2.

FIG. 6A: COH cells that do not excpress ROR1; FIG. 6Q: clone 16 (dashed line) and control (solid line).

DETAILED DESCRIPTION OF THE INVENTION

Figure 5:
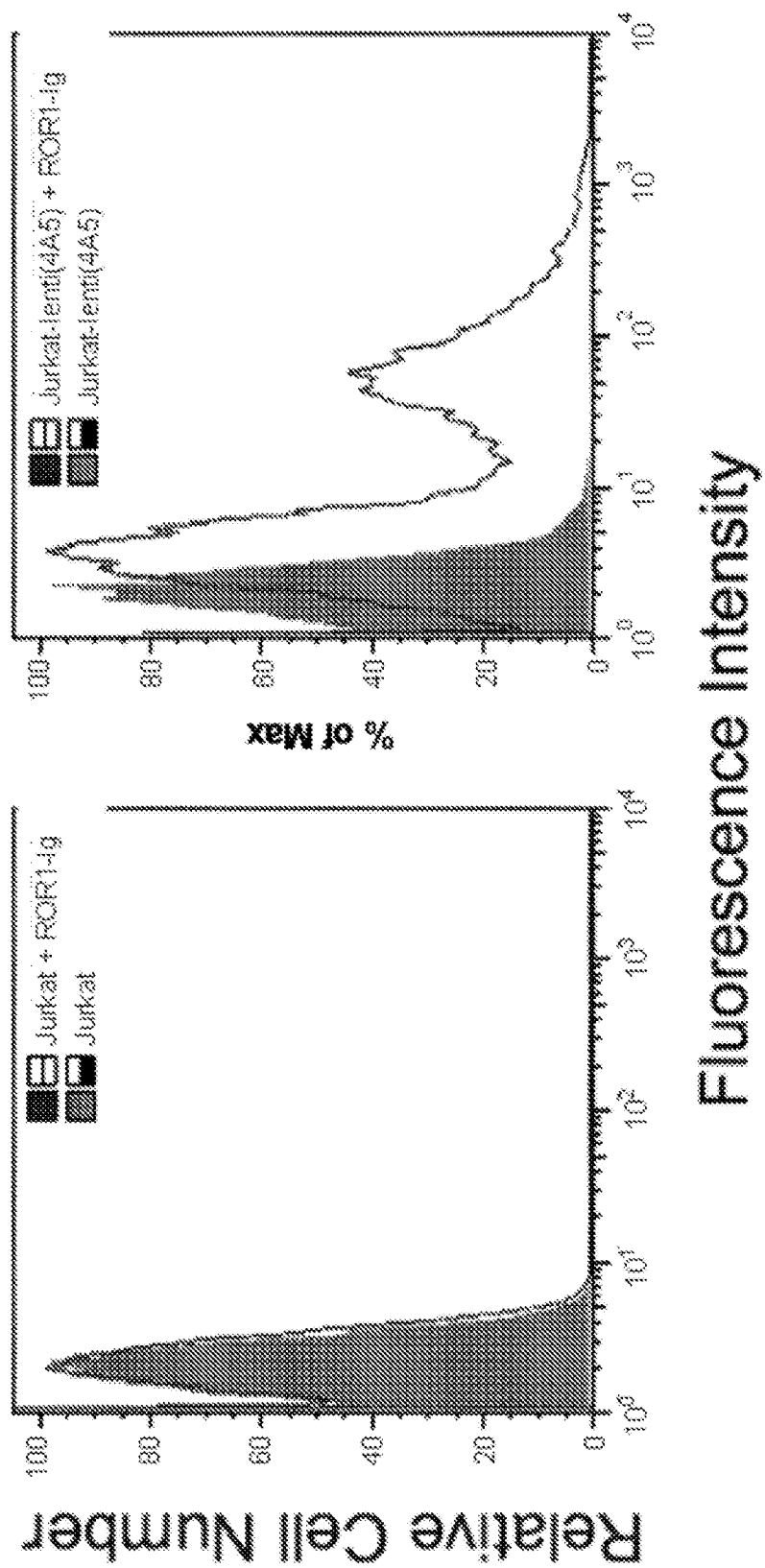
FIG. 5 shows plots of fluorescence intensity. The left plot shows intensity in a Jurkat T cell line and the right shows a Jurkat T cell line transduced to express an ROR.1 conjugate including anti-ROR1 mAb scFv, an IgG4 CH domain, a transmembrane domain of CD28, and a cytoplasmic domain of the zeta chain for a T-cell receptor (CD247) to generate a chimeric antigen receptor (ROR1-CAR). The shaded histogram indicates the autofluorescence of the unstained cells. The open histogram demonstrates the fluorescence of cells incubated with a soluble ROR1 protein (ROR:1-1g) and then stained with anti-Ig phycoerythrin (PE).

The present invention is based on the seminal generation of as anti-ROR1 scFv antibody and conjugates thereof including a biologically-active molecule. Such conjugates may comprise a chimeric receptor to direct T cells to respond to RORI cancer cells. Thus, the scFv may be used to target cells expressing ROR1 for therapeutic and diagnostic purposes.

Before the present methods are described, it is to be understood that this invention is not limited to particular compositions, methods, and experimental conditions described, as such compositions, methods, and conditions may vary. It is also to be understood that the terminology used herein is for purposes of describing particular embodiments only, and is not intended to be limiting, since the scope of the present invention will be limited only in the appended claims.

As used in this specification and the appended claims, the singular forms and "the" include plural references unless the context clearly dictates otherwise. Thus, for example, references to "the method" includes one or more methods, and/or steps of the type described herein which will become apparent to those persons skilled in the art upon reading this disclosure and so forth.

Unless defined otherwise, all technical and scientific terms used herein have the same meaning as commonly understood by one of ordinary skill in the art to which this invention belongs.

As shown previously, some patients developed IgG anti-CLL autoantibodies, which reacted with ROR1. These post-treatment antisera reacted with a protein of about.125 kD found in lysates of CLL cells or CHO-ROR1 cells, but not in lysates prepared from human blood lymphocytes of normal donors or non-transfected CHO cells. That these antisera reacted with RORI was corroborated via ELISA using a recombinant RORI fusion-protein. Because these antisera appeared specific for C1,1, cells, the expression of RORI on other adult tissues was studied. These studies revealed that expression of the ROR1 protein was restricted to CLL B-cells and was not found on the non-leukemic blood or marrow mononuclear cells of patients with CLL, potentially allowing for detection of CLL cells in the blood or marrow of patients with early-stage disease or minimal residual disease after therapy. Furthermore, ROR1 was not found on normal adult tissues or lymphoid cells, including CD5-positive B cells. As such, ROR1 appears to represent a specific leukemia-associated antigen (LAA).

ROR1 encodes a type I membrane receptor tyrosine kinase that initially was identified using oligonucleotide primers targeting sequences encoding amino acid sequences common to tyrosine kinase domains of different proteins. This protein appears highly conserved throughout evolution. ROR1. is evolutionary conserved among *Caenorhabditis elegans* (*C. elegans*), Aplysia, *Drosophila* melanogasier, *Xenopus*, mice, and humans. In rodents, RORI is expressed primarily in developing cephalic neural crest in the dorsal part of the diencephalons and mid-hind brain boundary during embryogenesis. Work in Caenorhabclitis *elegans* (*C. elegans*) indicated that the RORI-type kinases might be involved in the regulation of cell motility and in asymmetric cell division during embryogenesis.

Furthermore, the ROR protein in *C. elegans*, apparently has both kinase-dependent and kinase independent ROR-family receptor tyrosine kinases are characterized by the intracellular tyrosine kinase domains, highly related to those of the Trk-family receptor tyrosine kinases, and by the extracellular Frizzled-like cysteine-rich domains and kringle domains, which are common to receptors of the Wnt-family members. An ortholog to RORI, namely ROR2, has been found interact physically with Wnt5a to activate non-canonical Wnt-signaling.

As previously described, ROR1 interacts physically with Wnt5a. The interaction of RORI with Wnt5a was implicated in studies demonstrating that co-transfection of expression vectors encoding NF-κB reporter constructs, ROR1, and Wnt5a, but not other Wnt factors, could induce activation of NF-NB in a mutually dose-dependent fashion. This activity was determined to be independent of expression of LPR5/6, which ordinarily serves as a co-receptor for Wnt receptors. Physical interaction of ROR.1 with Wnt5a was observed using recombinant proteins, demonstrating that ROR1 has binding activity for Wnt5a independent of LPR.5/6. Nonetheless, Wnt5a apparently could not activate the canonical Wnt-signaling pathway when co-expressed with RORI in 293 cells.

Prior studies suggested that there is crosstalk between the Wnt-signaling pathway and the NF-κB-signaling pathway. β-catenin apparently can physically complex with NF-κB, resulting in reduction of NF-κB DNA binding, transactivation activity, and target gene expression. Whereas NB kinase-alpha (IκKa), involved in the phosphorylation of NF-κB2/p100, can phosphorylate and stabilize β-catenin, the kinase involved in activation of the canonical p50/p65 NF-κB pathway, namely IKκB, can enhance β-catenin degradation. Conceivably, the inability of RORI to activate the LEF/TCF-signaling may be secondary in part to its capacity to activate IKKP, leading to reduced stability of p-catenin and enhanced activity of NF-κB, which in itself could potentially play a role in cancer development. Furthermore, expression of ROR1 in CLL could contribute to the growth and/or survival of neoplastic cells induced by interaction with tissue stromal cells that might elaborate Wnt5a and other factors that activate NF-κB. Even though found circulating in the blood, CLL cells derive a survival benefit from interactions with marrow stromal cells, nurse-like cells, or dendritic cells, which are found in the leukemia-infiltrated marrow or lymphoid tissues of patients with this disease. It is noteworthy in this regard that dendritic cells have been found to express high-levels of Wnt5a.

It has also previously been determined that co-culture of CLL cells with CHO-Wnt5a cells maintained significantly higher viability over time in vitro than the same CLL cells co-cultured with CHO cells, which serves to control for other factors that might influence CLL-cell survival. These studies provides the first evidence that the survival of CLL cells can be enhanced in vitro by such Wnt factors, which presumably also might function to enhance the survival of CLL cells in lymphoid-tissue microenvironments containing cells that express Wnt5a.

Although there are other receptors for Wnt5a, ROR1 appears to be at least in part responsible for the survival-signal triggered by co-culture with Wnt5a-expressing CH() cells. This is indicated by findings that serum obtained after treatment with autologous Ad-CD154-CLL cells could neutralize the capacity of CHO-Wnt5a cells to enhance the survival of CLL cells over that of CLL cells co-cultured with CHO cells or CLL cells cultured alone. Absorption of such antiserum with CHO-ROR1 cells abrogated the capacity of the posttreatment serum to neutralize the activity of CHO-Wnt5a cells. Conceivably, such anti-ROR1 antibodies could be responsible for some of the size-reductions observed in the lymph nodes of patients who had received infusions of autologous Ad-CD154-CLL cells.

Whole antibodies that can react with native ROR1 protein have also been described in U.S. patent application Ser. No. 12/545,731 which is incorporated herein by reference. However, antibody variants or fragments that maintain specific binding with the native ROR1 protein are necessary as they provide increased flexibility in designing a wide variety of antibody conjugates that may be used for therapeutic and diagnostic purposes.

Figures 1, 2, 3:
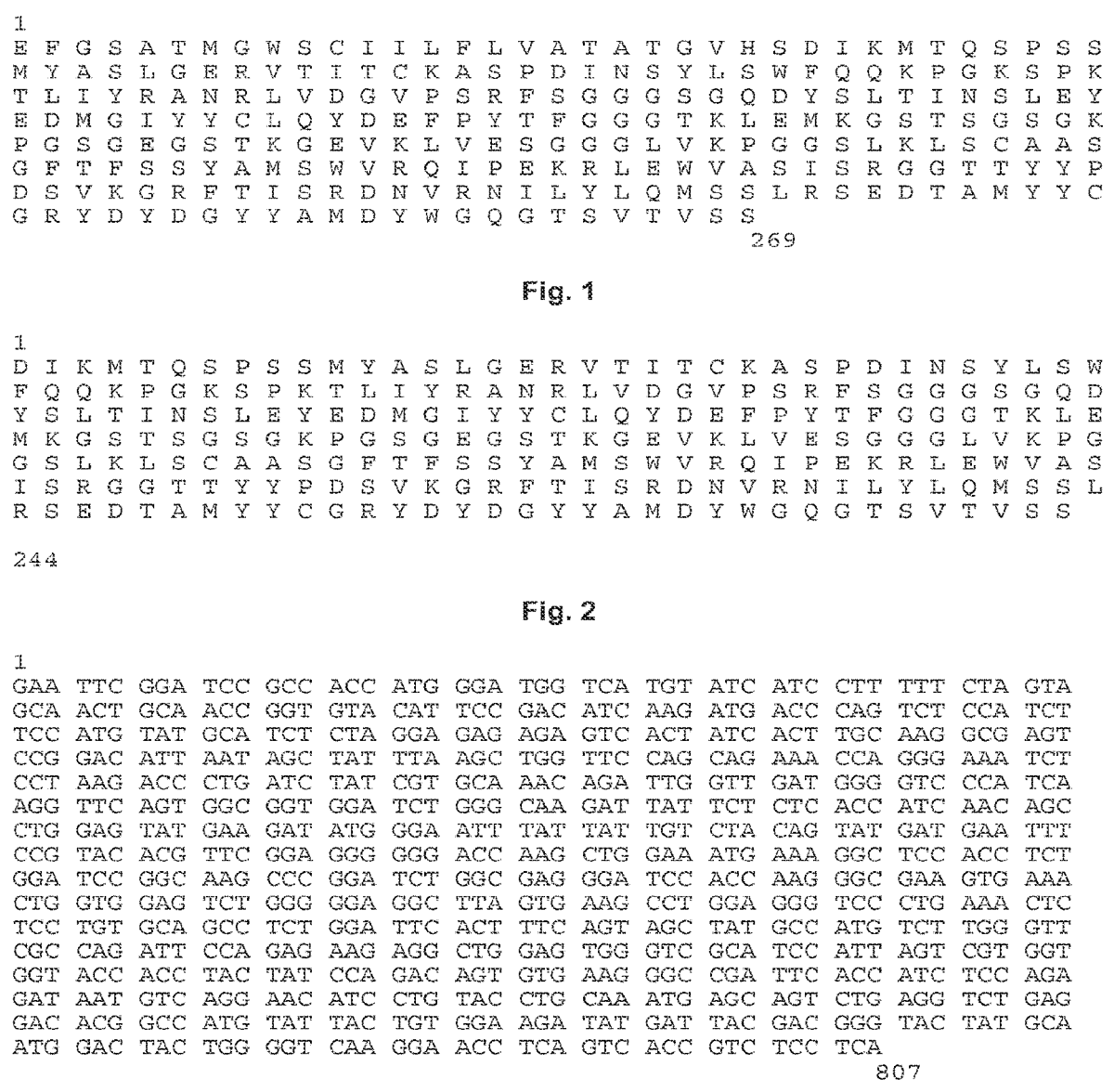

In one aspect, therefore, the present invention provides an antibody single-chain variable fragment (scFv) conjugate. The conjugate includes an scFv having an amino acid sequence at least 90%, 95% or 100% identical to SEQ ID NO: 1 or SEQ ID NO: 2 as shown in FIGS. 1 and 2, and a biologically active molecule. In exemplary embodiments, the conjugate and peptide has a binding specificity of an antibody as produced by a hybridoma having Accession No. PTA 8634 by the American Type Culture Collection.

In another aspect, the present invention provides an isolated peptide including an amino acid sequence at least 90%, 95% or 100% identical to SEQ ID NO: 1 or SEQ ID NO: 2.

A "conjugate" as used herein generally refers to a molecule which contains a peptide including an amino acid sequence at least 90%, 95% or 100% identical to SEQ ID NO: 1 or SEQ ID NO: 2, conjugated with a biologically active molecule. Typically, the conjugate is capable of being targeted to a cell expressing ROR1.

As used herein, the phrase "biologically active molecule" refers to a molecule that has a biological effect in a cell. In certain embodiments the active molecule may be an inorganic molecule, an organic molecule, a small organic molecule, a drug compound, a peptide, a polypeptide, a peptidomimetic, a nucleic acid molecule, a lipid, a drug compound, chemotherapeutic agent, a Liposome, an antagonist or an agonist.

For example, in various embodiments, the active molecule may be doxorubicin.

As used herein, "specific binding" refers to antibody binding to a predetermined antigen. Typically, the antibody binds with an affinity corresponding to a $K_D$ of about $10^{-8}$ M or less, and binds to the predetermined antigen with an affinity (as expressed by $K_D$) that is at least 10 fold less, and preferably at least 100 fold less than its affinity for binding to a nonspecific antigen (e.g., BSA, casein) other than the predetermined antigen or a closely-related antigen. Alternatively, the antibody can bind with an affinity corresponding to a $K_A$ of about $10^6$ $M^{-1}$, or about $10^7 M^{-1}$, or about $10^8 M^{-1}$, or $10^9 M^{-1}$ or higher, and binds to the predetermined antigen with an affinity (as expressed by $K_A$) that is at least 10 fold higher, and preferably at least 100 fold higher than its affinity for binding to a non-specific antigen (e.g., BSA, casein) other than the predetermined antigen or a closely-related antigen. In some embodiments the scFv antibody conjugate or peptide of the invention will have the same $K_A$ or $K_D$ as an antibody produced by the hybridoma having ATCC accession number PTA 8634.

The term "kd" ($sec^{-1}$), as used herein, is intended to refer to the dissociation rate constant of a particular antibody-antigen interaction. This value is also referred to as the off value. The term "$K_D$" ($M^{-1}$), as used herein, is intended to refer to the dissociation equilibrium constant of a particular antibody-antigen interaction.

The term "$k_a$" ($M^{-1}sec^{-1}$), as used herein, is intended to refer to the association rate constant of a particular antibody-antigen interaction. The term "$K_A$" (M), as used herein, is intended to refer to the association equilibrium constant of a particular antibody-antigen interaction.

Naturally occurring antibodies are generally tetramers containing two light chains and two heavy chains. Experimentally, antibodies can be cleaved with the proteolytic enzyme papain, which causes each of the heavy chains to break, producing three separate subunits. The two units that consist of a light chain and a fragment of the heavy chain approximately equal in mass to the light chain are called the Fab fragments (i.e., the "antigen binding" fragments). The third unit, consisting of two equal segments of the heavy chain, is called the Fc fragment. The Fe fragment is typically not involved in antigen-antibody binding, but is important in later processes involved in ridding the body of the antigen.

Because Fab and F(ab')$_2$ fragments are smaller than intact antibody molecules, more antigen-binding domains are available than when whole antibody molecules are used. Proteolytic cleavage of a typical IgG molecule with papain is known to produce two separate antigen binding fragments called Fab fragments which contain an intact light chain linked to an amino terminal portion of the contiguous heavy chain via by disulfide linkage. The remaining portion of the papain-digested immunoglobin molecule is known as the Fc fragment and consists of the carboxy terminal portions of the antibody left intact and linked together via disulfide bonds. If an antibody is digested with pepsin, a fragment known as an F(abs)$_2$ fragment is produced which lacks the Fc region but contains both antigen-binding domains held together by disulfide bonds between contiguous light and heavy chains (as Fab fragments) and also disulfide linkages between the remaining portions of the contiguous heavy chains (Handbook of Experimental Immunology. Vol 1: Immunochemistry, Weir, D. M., Editor, Blackwell Scientific Publications, Oxford (1986)).

As readily recognized by those of skill in the art, altered antibodies (e.g., chimeric, humanized, CDR-grafted, bifunctional, antibody polypeptide dieters (i.e., an association of two polypeptide chain components of an antibody, e.g., one arm of an antibody including a heavy chain and a light chain, or an Fab fragment including VL, VH, CL and CH antibody domains, or an Fv fragment comprising a VL domain and a VH domain), single chain antibodies (e.g., an scFv (i.e., single chain Fv) fragment including a VL domain linked to a VH domain by a linker, and the like) can also be produced by methods well known in the art.

Recombinant DNA methods have been developed which permit the production and selection of recombinant single chain Fv fragments (scFvs or scFv antibodies). Further, scFvs can be dimerized to produce a diabody. scFvs bind a specific epitope of interest and can be produced using any of a variety of recombinant bacterial phage-based methods, for example as described in Lowman et al. (1991) Biochemistry, 30, 10832-10838; Clackson et al. (1991) Nature 352, 624-628; and Cwirla et al. (1990) Proc. Natl. Acad. Sci. USA 87, 6378-6382. These methods are usually based on producing genetically altered filamentous phage, such as recombinant M13 or fd phages, which display on the surface of the phage particle a recombinant fusion protein containing the antigen-binding scFv antibody as the amino terminal region of the fusion protein and the minor phage coat protein g3p as the carboxy terminal region of the fusion protein. Such recombinant phages can be readily grown and isolated using well-known phage methods. Furthermore, the intact phage particles can usually be screened directly for the presence (display) of an antigen-binding scFv on their surface without the necessity of isolating the scFv away from the phage particle.

To produce an scFv, standard reverse transcriptase protocols are used to first produce cDNA from mRNA isolated from a hybridoma that produces an mAb for ROR-1 antigen. The cDNA molecules encoding the variable regions of the heavy and light chains of the mAb can then be amplified by standard polymerase chain reaction (PCR) methodology using a set of primers for mouse immunoglobulin heavy and light variable regions (Clackson (1991) Nature, 352, 624-628). The amplified cDNAs encoding mAb heavy and light chain variable regions are then linked together with a linker oligonucleotide in order to generate a recombinant scFv DNA molecule. The sdFc DNA is ligated into a filamentous phage plasmid designed to fuse the amplified cDNA sequences into the 5' region of the phage gene encoding the minor coat protein called g3p. Escherichia coli bacterial cells are than transformed with the recombinant phage plasmids, and filamentous phage grown and harvested. The desired recombinant phages display antigen-binding domains fused to the amino terminal region of the minor coat protein. Such "display phages" can then be passed over immobilized antigen, for example, using the method known as "panning", see Parmley and Smith (1989) Adv. Exp.: Med. Biol. 251, 215-218; Cwirla et al. (1990) Proc. Natl . . . Acad. Sci. USA. 87, 6378-6382, to adsorb those phage particles containing scFv antibody proteins that are capable of binding antigen. The antigen-binding phage particles can then be amplified by standard phage infection methods, and the amplified recombinant phage population again selected for antigen-binding ability. Such successive rounds of selection for antigen-binding ability, followed by amplification, select for enhanced antigen-binding ability in the scFvs displayed on recombinant phages. Selection for increased antigen-binding ability may be made by adjusting the conditions under which binding takes place to require a tighter binding activity. Another method to select for enhanced antigen-binding activity is to alter nucleotide sequences within the cDNA encoding the binding domain of the scFv and subject recombinant phage populations to successive rounds of selection for antigen-binding activity and amplification (see Lowman et al. (1991) Biochemistry 30, 10832-10838; and Cwirla. et al. (1990) Proc. Natl. Acad. Sci. USA 87, 6378-6382).

Once an scFv is selected, it can be produced in a free form using an appropriate vector in conjunction with E. coli strain HB2151. These bacteria actually secrete scFv in a soluble form, free of phage components (Hoogenboom et al. (1991) Nucl. Acids Res. 19, 41334137). The purification of soluble scFv from the HB2151 bacteria culture medium can be accomplished by affinity chromatography using antigen molecules immobilized on a solid support such as AFFI-GEL™ (BioRad, Hercules, Calif.).

Other developments in the recombinant antibody technology demonstrate possibilities for further improvements such as increased avidity of binding by polymerization of scFvs into dimers and tetramers (see Holliger et al. (1993) Proc. Natl. Acad. Sci. USA 90, 6444-6448).

Because scFvs are even smaller molecules than Fab or F(ab')2 fragments, they can be used to attain even higher densities of antigen binding sites per unit of surface area when immobilized on a solid support material than possible using whole antibodies, F(ab')2, or Fab fragments. Furthermore, recombinant antibody technology offers a more stable genetic source of antibodies, as compared with hybridomas. Recombinant antibodies can also be produced more quickly and economically using standard bacterial phage production methods.

To produce scFvs described herein recombinantly, nucleic acids encoding one is inserted into expression vectors. The light and heavy chains can be cloned in the same or different expression vectors. The teachings of U.S. Pat. No. 6,287,569 to Kipps et al., incorporated herein by reference in its entirety, and the methods provided herein can readily be adapted by those of skill in the art to create the scFvs of the present invention.

Expression vectors are typically replicable in the host organisms either as episomes or as an integral part of the host chromosome. E. coli is one procaryotic host particularly useful for expressing antibodies of the present invention. Other microbial hosts suitable for use include bacilli, such as Bacillus subtilus, and other enterobacteriaceae, such as Salmonella, Serratia, and various Pseudomonas species. In these prokaryotic hosts, one can also make expression vectors, which typically contain expression control sequences compatible with the host cell (e.g., an origin of replication) and regulatory sequences such as a lactose promoter system, a tryptophan (trp) promoter system, a beta-lactamase promoter system, or a promoter system from phage lambda. Other microbes, such as yeast, may also be used for expression. Saccharomyces is a preferred host, with suitable vectors having expression control sequences, such as promoters, including 3-phosphoglycerate kinase or other glycolytic enzymes, and an origin of replication, termination sequences and the like as desired. Mammalian tissue cell culture can also be used to express and produce the antibodies of the present invention (see, e.g., Wirmacker, From Genes to Clones VCH Publishers, N.Y., 1987). Eukaryotic cells are preferred, because a number of suitable host cell lines capable of secreting intact antibodies have been developed. Preferred suitable host cells for expressing nucleic acids encoding the immunoglobulins of the invention include: monkey kidney CV1 line transformed by SV40

(COS-7, ATCC CRL 1651); human embryonic kidney line; baby hamster kidney cells (BHK, ATCC CCL 10); Chinese hamster ovary-cells (CHO); mouse sertoli cells; monkey kidney cells (CV1 ATCC CCL 70); african green monkey kidney cells (VERO-76, ATCC CRL 1587); human cervical carcinoma cells (FIELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep 02, FIB 8065); mouse mammary tumor (MMT 060562, ATCC CCL51); and TRI cells.

The vectors containing the polynucleotide sequences of interest can be transferred into the host cell. Calcium chloride transfection is commonly utilized for prokaryotic cells, whereas calcium phosphate treatment or electroporation can be used for other cellular hosts (see, e.g., Sambrook et al., Molecular Cloning: A Laboratory Manual, Cold Spring Harbor Press, 2nd ed., 1989). After introduction of recombinant DNA, cell lines expressing immunoglobulin products are cell selected. Cell lines capable of stable expression are preferred (i.e., undiminished levels of expression after fifty passages of the cell line).

Once expressed, the scFv or other immunoglobulin forms of the present invention can be purified according to standard procedures of the art, including ammonium sulfate precipitation, affinity columns, column chromatography, gel electrophoresis and the like (see, e.g., Scopes, Protein Purification, Springer-Verlag, N.Y., 1982). Substantially pure immunoglobulins of at least about 90 to 95% homogeneity are preferred, and 98 to 99% or more homogeneity most preferred.

A labeled antibody or a detectably labeled antibody is generally an antibody (or antibody fragment which retains binding specificity), having an attached detectable label. The detectable label is normally attached by chemical conjugation, but where the label is a polypeptide, it could alternatively be attached by genetic engineering techniques. Methods for production of detectably labeled proteins are well known in the art. Detectable labels known in the art include radioisotopes, fluorophores, paramagnetic labels, enzymes (e.g., horseradish peroxidase), or other moieties or compounds which either emit a detectable signal (e.g., radioactivity, fluorescence, color) or emit a detectable signal after exposure of the label to its substrate. Various detectable label/substrate pairs (e.g., horseradish peroxidase/diaminobenzidine, avidin/streptavidin, luciferase/luciferin), methods for labeling antibodies, and methods for using labeled antibodies are well known in the art (see, for example, Harlow and Lane, eds., 1988, Antibodies: A Laboratory Manual, Cold Spring Harbor Laboratory Press, Cold Spring Harbor, N.Y.) Another technique which may also result in greater sensitivity consists of coupling the antibodies to low molecular weight haptens. These haptens can then be specifically detected by means of a second reaction. For example, it is common to use such haptens as biotin, which reacts with avidin, or dinitrophenyl, pyridoxal, and fluorescein, which can react with specific antihapten antibodies.

Antibodies may be humanized by replacing sequences of the Fv variable region which are not directly involved in antigen binding with equivalent sequences from human Fv variable regions. General reviews of humanized chimeric antibodies are provided by Morrison et al., (Science 229: 1202-1207 (1985)) and by Oi et al. (BioTechniques 4:214 (1986)). Those methods include isolating, manipulating, and expressing the nucleic acid sequences that encode all or part of immunoglobulin Fv variable regions from at least one of a heavy or light chain. Sources of such nucleic acid are well known to those skilled in the art and, for example, may be obtained from for example, an antibody producing hybridoma. The recombinant DNA encoding the humanized or chimeric antibody, or fragment thereof, can then be cloned into an appropriate expression vector.

Humanized antibodies can alternatively be produced by CDR substitution (U.S. Pat. No. 5,225,539; Jones, Nature 321:552-525 (1986); Verhoeyan et al., Science 239:1534 (1988); and Beidler, J. Immunol. 141:4053-4060 (1988)). Thus, in certain embodiments, the antibody used in the conjugate is a humanized or CDR-grafted form of an antibody produced by the hybridoma having ATCC accession number PTA. 2439. In other embodiments the antibody is a humanized or CDR-grafted form of antibody mAb 3E10. For example, the CDR regions can include amino acid substitutions such as 1, 2, 3, 4, 5, 6, 7, 8, 9, or 10 amino acid differences from those shown in the figures. In some instances, there are anywhere from 1-5 amino acid differences.

As used herein, reference to "an scFv antibody having the binding specificity of an antibody as produced by the hybridoma having ATCC accession number PTA. 8634" includes antibody fragments having at least 90% or 95% sequence identity to SEQ ID NO:1 or SEQ ID NO: 2 and retain the same binding specificity as that produced by the hybridoma having .ATCC accession number PTA 8634, such as variants modified by mutation to improve the utility thereof (e.g., improved ability to target specific cell types and the like). Such variants include those wherein one or more conservative substitutions are introduced into the heavy chain and/or the light chain of the scFv.

Such variants include those wherein one or more substitutions are introduced into the heavy chain nucleotide sequence and/or the light chain nucleotide sequence of the scFv. In some embodiments the variant has a light chain and/or heavy chain having a nucleotide sequence at least 80% or at least 90% or at least 95% identical to the nucleotide sequence set forth in SEQ ID NO: 3 or SEQ ID NO: 4.

In embodiments where the conjugates include polypeptides (i.e., protein conjugates), they may be designed as fusion protein conjugate such that the conjugate can be expressed in a host cell as a fusion protein. Alternatively, portions of the conjugate can be chemically linked by peptide bonds or by a chemical or peptide linker molecule of various types well known in the art as discussed further herein.

A variety of linkers may be used to link portions of the conjugates described herein. The term "degradable linker" as used herein, refers to linker moieties that are capable of cleavage under various conditions. Conditions suitable for cleavage can include but are not limited to pH, UV irradiation, enzymatic activity, temperature, hydrolysis, elimination, and substitution reactions, and thermodynamic properties of the linkage. The term "photolabile linker" as used herein, refers to linker moieties as are known in the art that are selectively cleaved under particular UV wavelengths. Compounds of the invention containing photolabile linkers can be used to deliver compounds to a target cell or tissue of interest, and can be subsequently released in the presence of a UV source.

The term "linker" as used herein is any bond, small molecule, or other vehicle which allows the substrate and the active molecule to be targeted to the same area, tissue, or cell, for example by physically linking the individual portions of the conjugate.

In certain embodiments, a cleavable or degradable linker may be used. In one embodiment the linker is a chemical bond between one or more substrates and one or more therapeutic moieties. Thus, the bond may be covalent or ionic. An example of a therapeutic complex where the linker is a chemical bond would be a fusion protein. In one embodiment, the chemical bond is acid sensitive and the pH sensitive bond is cleaved upon going from the blood stream (pH 7.5) to the transcytotic vesicle or the interior of the cell (pH about 6.0). Alternatively, the bond may not be acid sensitive, but may be cleavable by a specific enzyme or chemical which is subsequently added or naturally found in the microenvironment of the targeted site. Alternatively, the bond may be a bond that is cleaved under reducing conditions, for example a disulfide bond.

Alternatively, the bond may not be cleavable. Any kind of acid cleavable or acid sensitive linker may be used. Examples of acid cleavable bonds include, but are not limited to: a class of organic acids known as cipolycarboxylic alkenes. This class of molecule contains at least three carboxylic acid groups (COOH) attached to a carbon chain that contains at least one double bond. These molecules as well as how they are made and used is disclosed in Shen, et al. U.S. Pat. No. 4,631,190.

Alternatively, molecules such asamino-sulfhydryl crosslinking reagents which are cleavable under mildly acidic conditions may be used. These molecules are disclosed in U.S. Pat. No. 4,569,789.

Alternatively, the acid cleavable linker may be a time-release bond, such as a biodegradable, hydrolyzable bond. Typical biodegradable carrier bonds include esters, amides or urethane bonds, so that typical carriers are polyesters, polyamides, polyurethanes and other condensation polymers having a molecular weight between about 5,000 and 1,000,000. Examples of these carriers/bonds are shown in U.S. Pat. No. 4,356,166. Other acid cleavable linkers may be found in U.S. Pat. Nos. 4,569,789 and 4,631,190 or Blattner et al. (Biochemistry 24:1517-1524 (1984)). The linkers are cleaved by natural acidic conditions, or alternatively, acid conditions can be induced at a target site as explained in U.S. Pat. No. 4,171,563.

Examples of linking reagents which contain cleavable disulfide bonds (reducable bonds) include, but are not limited to "DPDPB", 1,4-di-[3'-(2'-pyridyldithio) propionamido] butane; "SADP", (N-succinimidyl (4-azidophenyl) 1,3'-dithiopropionate); "Sulfo-SADP" (Sulfosuccinimidyl (4-azi.dophenyldithio) propionate; "DSP"—Dithio bis (succinimidylproprionate); "DTSSP"—3,3'-Dithio bis(sulfosuccinimidylpropionate); "DTBP"—dimethyl 3,3dithiobispropionimidate-2HCI.

Examples of linking reagents cleavable by oxidation are "DST"—disuccinimidyl tartarate; and "Sulfo-DST"—disuccinimidyl tartarate.

Examples of non-cleavable linkers are "Sulfo-LC-SMPT"—(sulfosuccinimidyl 6-[alphamethyl-alpha-(2-pyridylthio)toluarnido}hexanoate; "SMPT"; ".ABH"—Azidobenzoyl hydrazide; "NHS-ASA"—N-Hydroxysuccinimidyl-4-azidosalicyclic acid; "SASD"—Sulfosuccinimidyl 2-(pazidosalicylamido) ethyl-1,3-dithiopropionate; ".APDP"—N-14-(p-azidosalicylamido) buthy)-3' (2'-pyidyldithio) propionamide; "BASED"—Bis-[13-(4-azidosalicylamido) ethyl] disulfide; "HSAB"—N-hydroxysuccinimidyl.-4 azi.dobenzoate; "APG"—p-Azidophenyl glyoxal monohydrate; "SANPAH"—N-Succiminidyl-6 (4'-azido-2'-mitrophenyl-amimo) hexanoate; "Sulfo-SANPAH"—Sulfosuccinimidyl6-(4'-azido-2'-nitrophenylamino) hexanoate; "ANaNOS" N-5-Azido-2-nitrobenzoyloxysuccinimide; "SAND"—Sulfosuccinimidyl-2-(m-azido-o-mitrobenzamido)-ethyl-1,3'-dithiopr-opionatc; "PNP-DTP"—p-nitrophenyl-2-diazo-3,3,3-trifluoropropionate; "SMCC"—Succinimidyl-4-(N-maleimidomethypcyclohexane-I-carboxylate; "Sulfo-SMCC"—Sulfosuccinirnidyl-4-(N maleimidomethyl) cyclohexane-I-carboxylate; "MBS" m-Maleimidobenzoyl-N-hydroxysuccinimide ester; "sulfo-MBS"—Maleimidobenzoyl-N-hydroxysulfosuccinimide ester; "SIAB"—N-Succinimidyl (4-iodoacetyl)aminobenzoate; "SulfSIAB"—N-Sulfosuccinimidyl (4-iodoacetyl)amino-benzoate; "SMPB"—Succinimidyl 4-(pmalenimidophenyl) butyrate; "Sulfo-SMPB"—Sulfosuccinirnidyl 4-(p-malenimidophenyl) butyrate; "DSS"—Disuccinimidyl suberate; "BSSS"—bis(sulfosuccinimidyl) suberate; "BMW—Bis maleimidohexane; "DFDNB"—1,5-difluoro-2,4-dinitrobenzene; "DMA"—dimethyl adipimidate 2HCI; "DMP"—Dimethyl pimelimidate-2HCI; "DMS"—dimethyl suberimidate-2-HC I; "SPDPN—succinimidyl-3-(2-pyridylthio) propionate; "Sulfo-HSAB"—Sulfosuccinimidyl 4-(pazidophenyl) butyrate; "Sulfo-SAPB"—Sulfosuccinimidyl 4-(p-azidophenylbutyrate); "ASIB"—1-9p-azidosalicylamido)-4-(iodoacetamido) butane; "ASBA"—4-(p-Azidosalicylamido) butylarnine.

In another embodiment the linker is a small molecule such as a peptide linker. In one embodiment the peptide linker is not cleavable. In a further embodiment the peptide linker is cleavable by base, under reducing conditions, or by a specific enzyme. In one embodiment, the enzyme is indigenous. Alternatively, the small peptide may be cleavable by an non-indigenous enzyme which is administered after or in addition to the therapeutic complex. Alternatively, the small peptide may be cleaved under reducing conditions, for example, when the peptide contains a disulfide bond. Alternatively, the small peptide may be pH sensitive.

The peptide linker may also be useful as a peptide tag (e.g., myc or His6 (SEQ ID NO: 5) or may be one or more repeats of the known linker sequence GGGGS (SEQ ID NO:6). The skilled artisan will recognize that the linker sequence may be varied depending on the polypeptide portions to be linked to form the conjugate. Additional peptide linkers and tags are known in the art, such as epitope tags, affinity tags, solubility enhancing tags, and the like. Examples of various additional tags and linkers that may be used with the present invention include, haemagglutinin (HA) epitope, myc epitope, chitin binding protein (CBP), maltose binding protein (MBP), glutathione-S-transferase (GST), calmodulin binding peptide, biotin carboxyl carrier protein (BCCP), FLAG octapeptide, nus, green fluorescent protein (GFP), thioredoxin (TRX), poly(NANP), V5, S-protein, streptavidin, SBP, poly(Arg), DsbA, c-myc-tag, HAT, cellulose binding domain, softag 1, softag3, small ubiquitin-like modifier (SUMO), and ubiquitin (Lib). Further examples include: poly(L-Gly), (Poly L-Glycine linkers); poly(L-Glu), (PolyL-Glutamine linkers); poly (1., -Lys), (Poly L-Lysine linkers). In one embodiment, the peptide linker has the formula (amino acid) n, where n is an integer between 2 and 100, preferably wherein the peptide comprises a polymer of one or more amino acids.

In a further embodiment the linker is a cleavable linker including, poly (ethylene glycol) (PEG) and a dipeptide, L-alanyl-L-valine (Ala-Val), cleavable by the enzyme thermolysin. This linker is advantageous because thermolysin-like enzyme has been reported to be expressed at the site of many tumors. Alternatively, an amino acid residue spacer may be used which contains the recognition site for the protease furin.

The chemical and peptide linkers can be bonded between the scFv and the active molecule by techniques known in the art for conjugate synthesis, i.e. using genetic engineering or chemically. The conjugate synthesis can be accomplished chemically via the appropriate antibody by classical coupling reactions of proteins to other moieties at appropriate functional groups.

Examples of the functional groups present in proteins and utilized normally for chemical coupling reactions are outlined as follows. The carbohydrate structures may be oxidized to aldehyde groups that in turn are reacted with a compound containing the group H2NNH—R (wherein R is the compound) to the formation of a C=NH—NH—R group. The thiol group (cysteines in proteins) may be reacted with a compound containing a thiol-reactive group to the formation of a thioether group or disulfide group. The free amino group (at the amino terminus of a protein or on a lysine) in amino acid residues may be reacted with a compound containing an electrophilic group, such as an activated carboxy group, to the formation of an amide group. Free carboxy groups in amino acid residues may be transformed to a reactive carboxy group and then reacted with a compound containing an amino group to the formation of an amide group.

The linker or biologically active molecule may alternatively be a liposome or nanoparticle containing a biologically active molecule. Many methods for the preparation of liposomes are well known in the art. For example, the reverse phase evaporation method, freezethaw methods, extrusion methods, and dehydration-rehydration methods (see, Storm et al., PSTT 1:19-31 (1998)). For use in cancer immunotherapy, PEGylated or "stealth" liposomes are especially useful. For example, such liposomes allow for delivery of highly charged therapeutic molecules such as siRNA into cells.

The liposomes may be produced in a solution containing the active molecule, such as doxorubicin, so that the substance is encapsulated during polymerization. Alternatively, the liposomes can be polymerized first, and the biologically active substance can be added later by resuspending the polymerized liposomes in a solution of a biologically active substance and treating with sonication to affect encapsulation of the active molecule. The liposomes can be polymerized in the presence of the substrate such that the substrate becomes a part of the phospholipid bilayer. In one embodiment, the liposome contains the active molecule on the inside and the substrate on the outside.

The liposomes contemplated in the present invention can comprise a variety of structures. For example, the liposomes can be multilamellar large vesicles (MLV), oligolamellar vesicles (OLV), unilamellar vesicles (UV), small unilamellar vesicles (SUV), medium sized unilamellar vesicles (MUV), large unilamellar vesicles (LUV), giant unilamellar vesicles (GUY), or multivesicular vesicles (MVV). Each of these liposome structures are well known in the art (see, Storm et al., PSTT 1:19-31 (1998)).

In one embodiment, the liposome is a "micromachine" that evulses pharmaceuticals for example by the application of specific frequency radio waves.: In another embodiment, the liposomes can be degraded such that they will release the active molecule in the targeted cell, for example, the liposomes may be acid or alkaline. sensitive, or degraded in the presence of a low or high pH, such that the active molecule is released within the cell. Alternatively, the liposomes may be uncharged so that they will be taken up by the targeted cell. The liposomes may also be pH sensitive or sensitive to reducing conditions.

One type of liposome which may be advantageously used in the present invention is that identified in U.S. Pat. No. 6,004,534. In this application a method of producing modified liposomes which are prepared by polymerization of double and triple bond-containing monomeric phospholipids is disclosed. These liposomes have surprisingly enhanced stability against the harsh environment of the gastrointestinal tract. Thus, they have utility for oral and/or mucosal delivery of the active molecule. It has also been shown that the liposomes may be absorbed into the systemic circulation and lymphatic circulation. The liposomes are generally prepared by polymerization (i.e., radical initiation or radiation) of double and triple bond-containing monomeric phospholipids.

Advantageously, in other embodiments of the present invention, the linker can also be a liposome having a long blood circulation time. Such liposomes are well known in the art (see U.S. Pat. Nos. 5,013,556; 5,225,212; 5,213,804; 5,356,633; and 5,843,473). Liposomes having long blood circulation time are characterized by having a portion of their phosphoslipids derivatized. with polyethylene glycol (PEG) or other similar polymer. In some embodiments, the end of the PEG molecule distal to the phospholipid may be activated so as to be chemically reactive. Such a reactive PEG molecule can be used to link a substrate to the liposome. One example of a reactive PEG molecule is the maleimide derivative of PEG described in U.S. Pat. No. 5,527,528).

Alternatively, the linker may be a microcapsule, a nanoparticle, a magnetic particle, and the like (see Kumar, J. Pharm. Sci. 2:234-258 (2000); and Gill et al., Trends Biotechnol. 18(11):469-79 (2000)), with the lipophilic active molecule on or in the container, and the container functioning as the linker in the therapeutic complex.

Alternatively, the linker may be a photocleavable linker. For example, a 1-2-(nitrophenyl)ethyl moiety can be cleaved using 300 to 360 urn light. It can be envisioned that the photocleavable linker would allow activation and action of the drug in an even more specific area, for example a particular part of the organ. The light could be localized using a catheter into the vessel. Alternatively, light may be used to localize treatment to a specific part of the digestive tract and the light may be manipulated through a natural orifice to the area. Alternatively, the light can be surgically manipulated to the area.

Alternatively, the linker may not be cleavable, but the active molecule or substrate is. An example of this is when the active molecule is a prodrug and the enzyme which cleaves the prodrug is administered with the therapeutic complex. Alternatively, the enzyme is part of the therapeutic complex or indigenous and the prodrug is administered separately. Preferably, the enzyme or prodrug which is administered separately is administered within about 48 hours of the first administration. Alternatively, the prodrug or enzyme which is administered separately may be administered between about 1 min and 24 hours, alternatively between about 2 min and 8 hours. The prodrug or enzyme which is administered separately, may be readministered at a later date and may continue to be administered until the effect of the drug is no longer needed.

In certain embodiments, the subject conjugates can be delivered via an expression construct to cells, including a nucleic acid that provides a coding sequence for a therapeutic protein. For instance, the expression construct can encode a therapeutic protein that is secreted by the transduced cell.

As used herein, the term "nucleic acid" refers to polynucleotides such as deoxyribonucleic acid (DNA), and, where appropriate, ribonucleic acid (RNA). The term should also be understood to include, as appropriate to the context or as applicable to the embodiment being described, both single-stranded polynucleotides (such as antisense) and double-stranded polynucleotides (such as siRNAs).

A "protein coding sequence" or a sequence that "encodes" a particular polypeptide or peptide, is a nucleic acid sequence that is transcribed (in the ease of DNA) and is translated (in the case of mRNA) into a polypeptide in vitro or in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, cDNA from prokaryotic or eukaryotic mRNA, genomic DNA sequences from prokaryotic or eukaryotic DNA, and even synthetic DNA sequences. A transcription termination sequence will usually be located 3' to the coding sequence.

As used herein, the term "vector" refers to a nucleic acid molecule capable of transporting another nucleic acid to which it has been linked. One type of vector is a genomic integrated vector, or "integrated vector," which can become integrated into the chromosomal DNA of the host cell. Another type of vector is an episomal vector, e.g., a nucleic acid capable of extra-chromosomal replication. Vectors capable of directing the expression of genes to which they are operatively linked are referred to herein as "expression vectors." In the present specification, "plasmid" and "vector" are used interchangeably unless otherwise clear from the context. In the expression vectors, regulatory elements controlling transcription can be generally derived from mammalian, microbial, viral or insect genes. The ability to replicate in a host, usually conferred by an origin of replication, and a selection gene to facilitate recognition of transformants may additionally be incorporated. Vectors derived from viruses, such as retroviruses, adenoviruses, and the like, may be employed.

In one embodiment, the present invention provides a method of producing a protein. The method includes transforming a host cell with an expression construct, and culturing the host cell under conditions suitable for producing the conjugate. in various embodiments, the expression construct includes a nucleic acid molecule encoding a protein conjugate including an scFv and a peptide, wherein the scFv includes an amino acid sequence at least 90%, at least 95% or 100% identical to SEQ ID NO: 1 or SEQ ID NO: 2.

Vectors suitable for use in preparation of proteins and/or protein conjugates include those selected from baculovirus, phage, plasmid, phagemid, cosmid, fosmid, bacterial artificial chromosome, viral DNA, P1-based artificial chromosome, yeast plasmid, and yeast artificial chromosome. For example, the viral DNA vector can be selected from vaccinia, adenovirus, foul pox virus, pseudorabies and a derivative of SV40. Suitable bacterial vectors for use in practice of the invention methods include pQE70™, pQE60, pQE-9, pBLUESCRIPT SK, pBLUESCRIPT™ KS, pTRC99a™, pKK223-3™, pDRS4O™, PAC™ and pRIT2T™. Suitable eukaryotic vectors for use in practice of the invention methods include pWLNEO™, pXTI™, pSG5™, pSVK3™, pBPV™, pMSG™, and pSVLSV40™. Suitable eukaryotic vectors for use in practice of the invention methods include pWLNEO™, pXTI™, pSG5™, pSVK3™, pBPV™, pMSG™, and pSVLSV40™.

Those of skill in the art can select a suitable regulatory region to be included in such a vector, for example from lacI, lacZ, T3, 17, apt, lambda PR, PL, trp, CMV immediate early, HSV thymidine kinase, early and late SV40, retroviral LTR, and mouse metallothionein-I regulatory regions.

Host cells in which the vectors containing the polynucleotides encoding the protein conjugates can be expressed include, for example, a bacterial cell, a eukaryotic cell, a yeast cell, an insect cell, or a plant cell. For example, *E. coli, Bacillus, Streptomyces, Pichia pastoris, Salmonella typhimurium, Drosophila* S2, *Spodoptera* SJ9, CHO, COS (e.g. COS-7), or Bowes melanoma cells are all suitable host cells for use in practice of the invention methods.

Conjugates in which the biologically active molecule is an antibody or sacFv molecule may be generated using methods known in the art. For example, methods for attaching a drug or other small molecule pharmaceutical to protein include bifunctional chemical linkers such as N-suc cinimidyl (4-iodoacetyl)-aminobenzoate; sulfosuccinimidyl(4-iodoacetyl)-aminobenzoate; 4-succinimidyl-oxycarbonyl-a-(2-pyridyldithio) toluene; sulfosuccinimidyl-6-[a-methyl-a-(pyridyldithiol)-toluamido]hexanoate; N-succinimidyl-3-(2-pyridyldithio)-proptionate; succinimidyl-643(4-2-pyridyldithio)-proprionamidoThexanoate; sulthsuccinimidyl-6-[3(4-2-pyridyldithio)-propionamido-bexanoate; 3-(2-pyridyldithio)-propionyl hydrazide, Ellman's reagent, dichlorotriazinic acid, S-(2-thiopyridyl)-L-cysteine, and the like. Further bifunctional linking molecules are disclosed in U.S. Pat. Nos. 5,349,066; 5,618,528; 4,569, 789; 4,952,394; and 5,137,877, each of which is incorporated herein by reference in its entirety.

In certain embodiments, a conjugate of the present invention may further contain a detectable label. Such labels are known in the art and include radio-isotopes and fluorescent labels. As such, internalization of a compound evidencing passage through transporters can be detected by detecting a signal from within a cell from any of a variety of reporters. The reporter can be a label such as a fluorophore, a chromophore, a radioisotope. Confocal imagining can also be used to detect internalization of a label as it provides sufficient spatial resolution to distinguish between fluorescence on a cell surface and fluorescence within a cell; alternatively, confocal imaging can be used to track the movement of compounds over time. In another approach, internalization of a compound is detected using a reporter that is a substrate for an enzyme expressed within a cell. Once the complex is internalized, the substrate is metabolized by the enzyme and generates an optical signal or radioactive decay that is indicative of uptake. Light emission can be monitored by commercial PMT-based instruments or by CCD-based imaging systems. In addition, assay methods utilizing LCMS detection of the transported compounds or electrophysiological signals indicative of transport activity are also employed.

In some embodiments, the conjugates of the present invention may include a biologically active molecule that is a nucleic acid molecule or analog thereof. As such the conjugates may be utilized to deliver nucleic acids, or analogs thereof, to a targeted tissue or cell type. For example, protein expression can be specifically down-regulated using oligonucleotides such as, for example, antisense molecules, locked nucleic acids (LNA), peptide nucleic acids (PNA), morpholino nucleic acids and small interfering RNAs (siRNA) of various chemistries. Alternatively, expression constructs may be delivered to cells, to induce expression of a desired gene product.

The expression construct that is delivered typically is part of a vector in which a regulatory element such as a promoter is operably linked to the nucleic acid of interest. The promoter can be constitutive or inducible. Non-limiting examples of constitutive promoters include cytomcgalovirus (CMV) promoter and the Rous sarcoma virus promoter. As used herein, "inducible" refers to both up-regulation and down regulation. An inducible promoter is a promoter that is capable of directly or indirectly activating transcription of one or more DNA sequences or genes in response to an inducer. In the absence of an inducer, the DNA sequences or genes will not be transcribed. The inducer can be a chemical agent such as a protein, metabolite, growth regulator, phenolic compound, or a physiological stress imposed directly by, for example heat, or indirectly through the action of a pathogen or disease agent such as a virus. The inducer also can be an illumination agent such as light and light's various aspects, which include wavelength, intensity, fluorescence, direction, and duration.

An example of an inducible promoter is the tetracycline (tet)-on promoter system, which can be used to regulate transcription of the nucleic acid. In this system, a mutated Tet repressor (TetR) is fused to the activation domain of herpes simplex VP 16 (transactivator protein) to create a tetracycline-controlled transcriptional activator (tTA), which is regulated by tet or doxycycline (dox). in the absence of antibiotic, transcription is minimal, while in the presence of tet or dox, transcription is induced. Alternative inducible systems include the ecdysone or rapamycin systems. Ecdysonc is an insect molting hormone whose production is controlled by a heterodimer of the ecdysone receptor and the product of the ultraspiracle gene (USP). Expression is induced by treatment with ecdysone or an analog of ecdysone such as muristerone A.

Additional regulatory elements that may be useful in vectors, include, but are not limited to, polyadenylation sequences, translation control sequences (e.g., an internal ribosome entry segment, IRES), enhancers, or introns. Such elements may not be necessary, although they may increase expression by affecting transcription, stability of the mRNA, translational efficiency, or the like. Such elements can be included in a nucleic acid construct as desired to obtain optimal expression of the nucleic acids in the ce1.1(s). Sufficient expression, however, may sometimes be obtained without such additional elements.

Vectors also can include other elements. For example, a vector can include a nucleic acid that encodes a signal peptide such that the encoded polypeptide is directed to a particular cellular location (e.g., a signal secretion sequence to cause the protein to be secreted by the cell) or a nucleic acid that encodes a selectable marker. Non-limiting examples of selectable markers include puromycin, adenosine dcaminasc (ADA), aminoglycosidc phosphotransferase neo, 6418, APH), dihydrofolate reductase (DHFR), hygromycin-B-phosphtransferase, thyrnidine kinase (TK), and xanthin-guanine phosphoribosyltransferase (XGPRT). Such markers are useful for selecting stable transformants in culture.

Viral vectors can be used to form the conjugates, and include adenovinis, adeno-associated virus (AAV), retroviruses, lentiviruses, vaccinia virus, measles viruses, herpes viruses, and bovine papilloma virus vectors (see, Kay et al., I'roc. Natl. Acad. Sci. USA. 94:12744-12746 (1997) for a review of viral and non-viral vectors). Viral vectors are modified so the native tropism and pathogenicity of the virus has been altered or removed. The genome of a virus also can be modified to increase its infectivity and to accommodate packaging of the nucleic acid encoding the polypeptide of interest.

Non-viral vectors can also be used in the subject conjugates. To further illustrate, in one embodiment, the mammalian serum protein that is encoded by the vector is selected from the group consisting of a tissue-type plasminogen activator, a receptor of a tissue-type plasminogen activator, a streptokinase, a staphylokinase, a urokinase, and coagulation factors. The invention also provides a method for treating associated with the formation of clots in its circulation, including the step of administering to the mammal a conjugate that causes the recombinant expression and secretion into the blood, such as from transduced muscle cells, of a therapeutically effective amount of such a mammalian serum protein.

An aptamer is a DNA or RNA molecule that has been selected from a random or biased pool of oligonucleic acids, based on its ability to bind to a target molecule. Aptamers can be selected which bind nucleic acids, proteins, small organic compounds and specific cell surfaces, and several have been developed which bind to proteins which are associated with disease states. Aptamers are in general more easily manufactured and are more amenable to chemical modification than are antibodies, and they can be "evolved" for tighter binding to the target by an iterative process of random modification and affinity-based selection. The evolved aptamers often have antibody-like specificities, and are therefore expected to have utility in those applications, such as therapeutics and in vitro and in vivo diagnostics.

According to another embodiment of the invention, there are provided methods for treating a disease or disorder in a cell or tissue expressing ROR1, especially CLL. The method includes administering to a patient a scFv conjugate, coding sequence, vector or aptamer of the present invention.

In a related embodiment of the invention, there are provided methods for targeting a cell or tissue expressing ROR1, especially CLL. cells. The method includes contacting the cell or tissue with an scFv conjugate, coding sequence, vector or aptamer of the present invention.

The scFv antibody conjugates, coding sequences, vectors or aptamers of the present invention may be employed as therapeutic or prophylactic pharmacological agents in any subject in which it is desirable to administer, in vitro, ex vivo, or in vivo the subject antagonists that bind ROR1; e.g., to treat CLL. Typical subjects for treatment or management according to the methods herein are subjects presenting with a ROR.1 cancer; e.g., CLL. The antagonists described herein specifically recognize ROR1 protein, found in lymphoma samples but not expressed in cells of normal adults, and therefore can be used for detecting and/or neutralizing these biomolecules, and/or blocking their interactions with other biomolecules, in vitro or in vivo.

In certain embodiments, the methods herein may be used to target therapeutic antibodies, or nucleic acids encoding them, to particular target cells. The antibodies may be, for example, monoclonal antibodies, polyclonal antibodies, single-chain antibodies, or bi-specific antibodies. Therapeutic antibodies are known to include, but are not limited to, Anti_EGFr antibodies (e.g., panitumamab, Erbitux (cetuximab), matuzumab, IMC-11F 8, TheraCiM hR3), denosumab, .Avastin (bevacizumab), Anti-I-10F antibodies, Humira (adalimumab), Anti-Ang-2 antibodies, Herceptin (trastuzumab), Remicade (infliximab), Anti-CD20 antibodies, rituximab, Synagis (paliviztunab), Mylotarg (gemluzumab oxogainicin), Raptiva (eializumab), Tysabri (natalizumab), Zenapax (dacliximab), NeutroSpec (Technetium ($^{99m}$Tc) fanolesomab), tocilizumab, ProstaScint (Indium-Ill labeled Capromab Pendetide), Bexxar (tositumomab), Zevalin (ibritumomab tiuxetan (IDEC-Y2B8) conjugated to yttrium 90), Xolair (omalizumab), MabThera. (Rituximab), ReoPro (abciximab), MabCampath (alemtuzumab), Simulect (basiliximab), LeukoScan (sulesomab), CEA-Scan (arcitumomab), Verluma (nofetumomab), Panorex (Edrecolomab), alemtuzumab, CUP 870, and natalizumab.

In certain therapeutic embodiments, the selected scFv antibody conjugate, coding sequence, vector or aptamer may be administered alone, or in combination with, or conjugated to, one or more combinatorial therapeutic agents. When the scFV molecules described herein are administered alone as therapeutic agents, they may exert a beneficial effect in the subject by a variety of mechanisms. For example, in certain embodiments, scFv antibody conjugates that specifically bind ROR1 are purified and administered to a patient to neutralize one or more forms of RORI, to block one or more activities of ROR1, or to block or inhibit an interaction of one or more forms of ROR1 with another biomolecule; e.g., to treat CLL or other ROR.I cancers.

As discussed herein, the scFV molecules of the invention may include humanized antibodies, and can be combined for therapeutic use with additional active or inert ingredients, e.g., in conventional pharmaceutically acceptable carriers or diluents, e.g., immunogenic adjuvants, and optionally with adjunctive or combinatorially active molecules such as anti-inflammatory and anti-fibrinolytic drugs.

In other embodiments, the scFv conjugates, coding sequences, vectors or aptamers described herein are coordinately administered with, co-formulated with, or coupled to (e.g., covalently bonded) a combinatorial therapeutic agent, for example a radionuclide, a differentiation inducer, a drug, or a toxin. Various known radionuclides can be employed, that are well known in the art. Useful drugs for use in such combinatorial treatment formulations and methods include methotrexate, and pyrimidinc and purinc analogs. Suitable differentiation inducers include phorbol esters and butyric acid. Suitable toxins include ricin, abrin, diptheria toxin, cholera toxin, gelonin, *Pseudomonas* exotoxin, *Shigella* toxin, and pokeweed antiviral protein. These combinatorial therapeutic agents can be coupled to an anti-ROR1 antibody either directly or indirectly (e.g., via a linker group). A. direct reaction between an agent and an antibody is possible when each possesses a substituent capable of reacting with the other. For example, a nucleophilic group, such as an amino or sulfhydryl group, on one may be capable of reacting with a carbonyl-containing group, such as an anhydride or an acid halide, or with an alkyl group containing a good leaving group (e.g., a halide) on the other. Alternatively, it may be desirable to couple a combinatorial therapeutic agent and an antibody via a linker group as a spacer to distance an antibody from the combinatorial therapeutic agent in order to avoid interference with binding capabilities. A linker group can also serve to increase the chemical reactivity of a substituent on an agent or an antibody, and thus increase the coupling efficiency. It will be further evident to those skilled in the art that a variety of bifunctional or polyfunctional reagents, both homo- and hetero-functional (such as those described in the catalog of the Pierce Chemical Co., Rockford, 1.11.), may be employed as a linker group. Coupling may be affected, for example, through amino groups, carboxyl groups, sulfhydryl groups or oxidized carbohydrate residues.

In carrying out various assay, diagnostic, and therapeutic methods of the invention, it is desirable to prepare in advance kits comprises a combination of scFv conjugate or peptide as described herein with other materials. For example, in the case of sandwich enzyme immunoassays, kits of the invention may contain an scFv antibody that specifically binds ROR1 optionally linked to an appropriate carrier, a freeze-dried preparation or a solution of an enzyme-labeled monoclonal antibody which can bind to the same antigen together with the monoclonal antibody or of a polyclonal antibody labeled with the enzyme in the same manner, a standard solution of purified ROR.1, a buffer solution, a washing solution, pipettes, a reaction container and the like. In addition, the kits optionally include labeling and/or instructional materials providing directions (i.e., protocols) for the practice of the methods described herein in an assay environment. While the instructional materials typically comprise written or printed materials, they are not limited to such. Any medium capable of storing such instructions and communicating them to an end user is contemplated. Such media include, but arc not limited to electronic storage media (e.g., magnetic discs, tapes, cartridges, chips), optical media (e.g., CD ROM), and the like. Such media may include addresses to internet sites that provide such instructional materials.

Having described the invention in detail, it will be apparent that modifications, variations, and equivalent embodiments are possible without departing the scope of the invention defined in the appended claims. Furthermore, it should be appreciated that all examples in the present disclosure are provided as non-limiting examples.

Example 1

Generation of an scFv Construct

This example illustrates generation of an scFv antibody conjugate of the present invention.

The scFV having SEQ ID NO: 3 was inserted upstream of the sequence encoding an IgG4 CH domain, the transmembrane domain of CD28 and cytoplasmic domain of the zeta chain for the Ti-cell receptor (CD247) to generate a chimeric antigen receptor (CAR).

The construct was inserted into a lenti-virus vector for transduction of T cells (Jurkat). The T cells were examined for their capacity to bind a soluble ROR1 protein (RORI-1g). Cell-bound ROR1-11g could be detected by staining the cells with an anti-Ig antibody that was labeled with a fluorescence dye, phycoerythrin (PE). This allowed monitoring of changes in fluorescence of the T cells caused by binding the ROR I protein using flow cytometry.

The results are shown in FIG. 5.

Example 2 scFV Targeting of ROR1 Expression by Lymphocytic B Cells

Figure 6A:
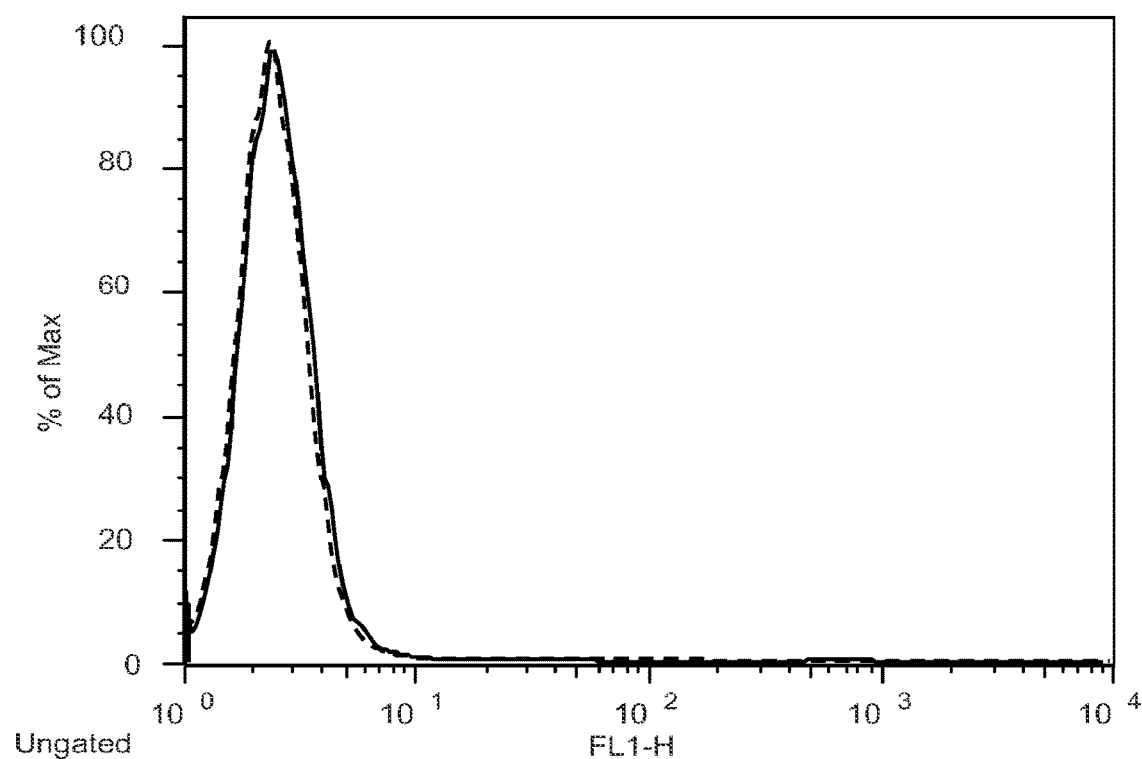
FIGS. 6A-6Q show the results of FA.CS analysis for PC DNA 3.1. CH2CH3 stable scFV clones targeting of Endemic African Burkitt's lymphoma B cells (EW36). Results for non-ROR I expressing CH:0 cells are provided for comparison. Figure legends.
Figure 6B:
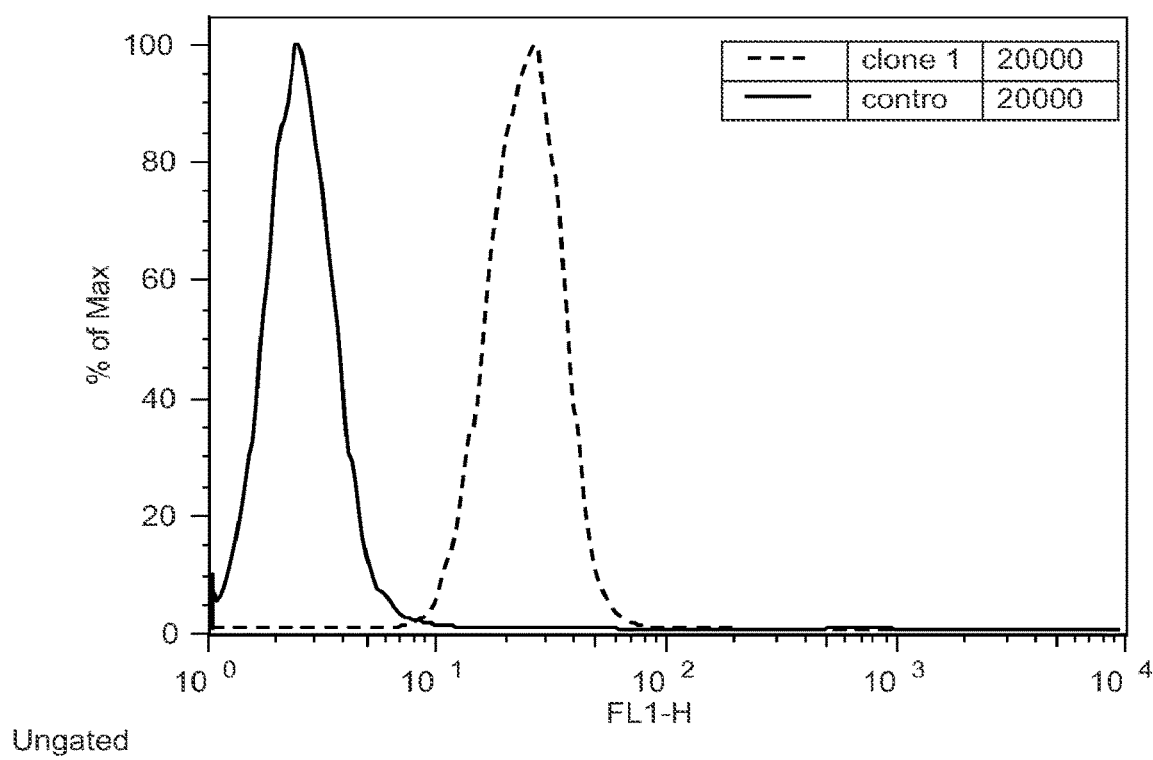
FIG. 6B: clone 1 (dashed lines) and control (solid line)
Figure 6C:
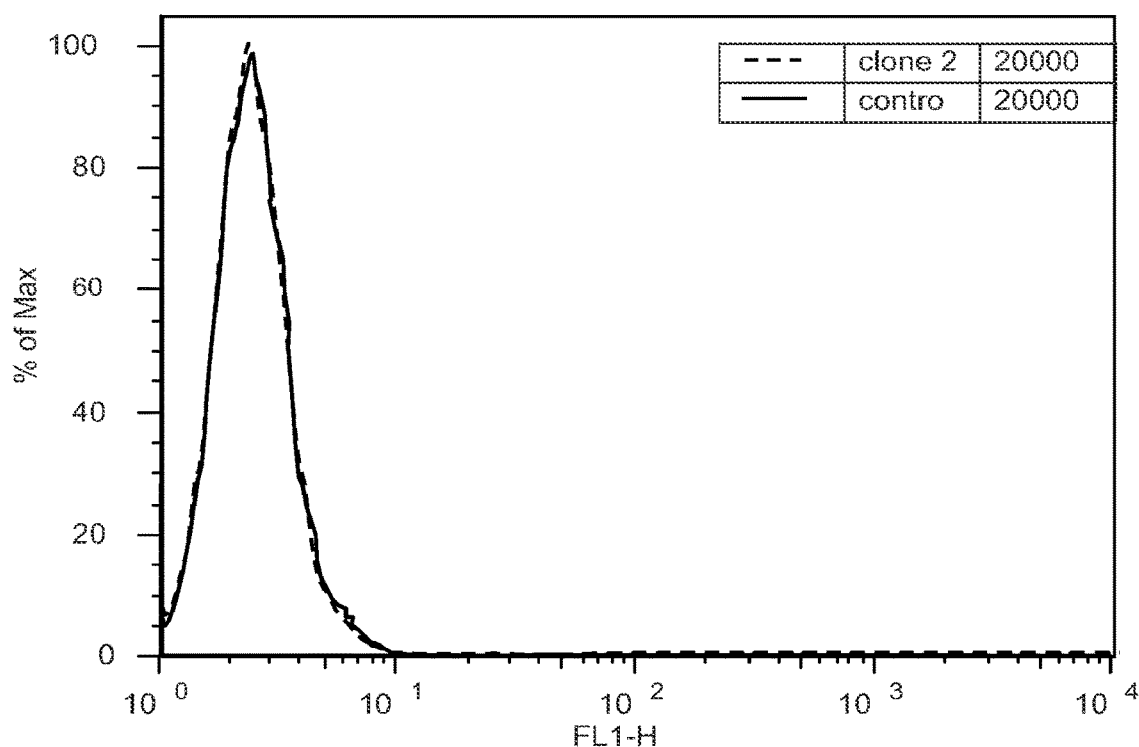
FIG. 6C: clone 2 (dashed line) and control (solid line)
Figure 6D:
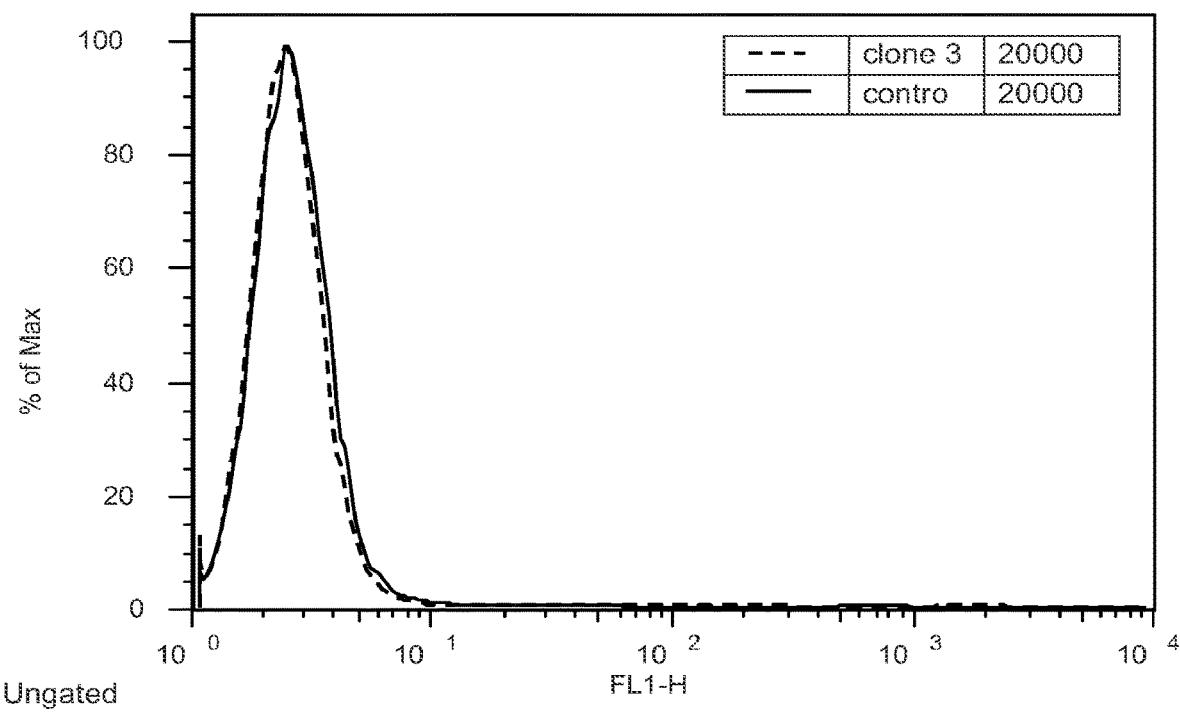
FIG. 6D: clone 3 (dashed line) and control (solid line)
Figure 6E:
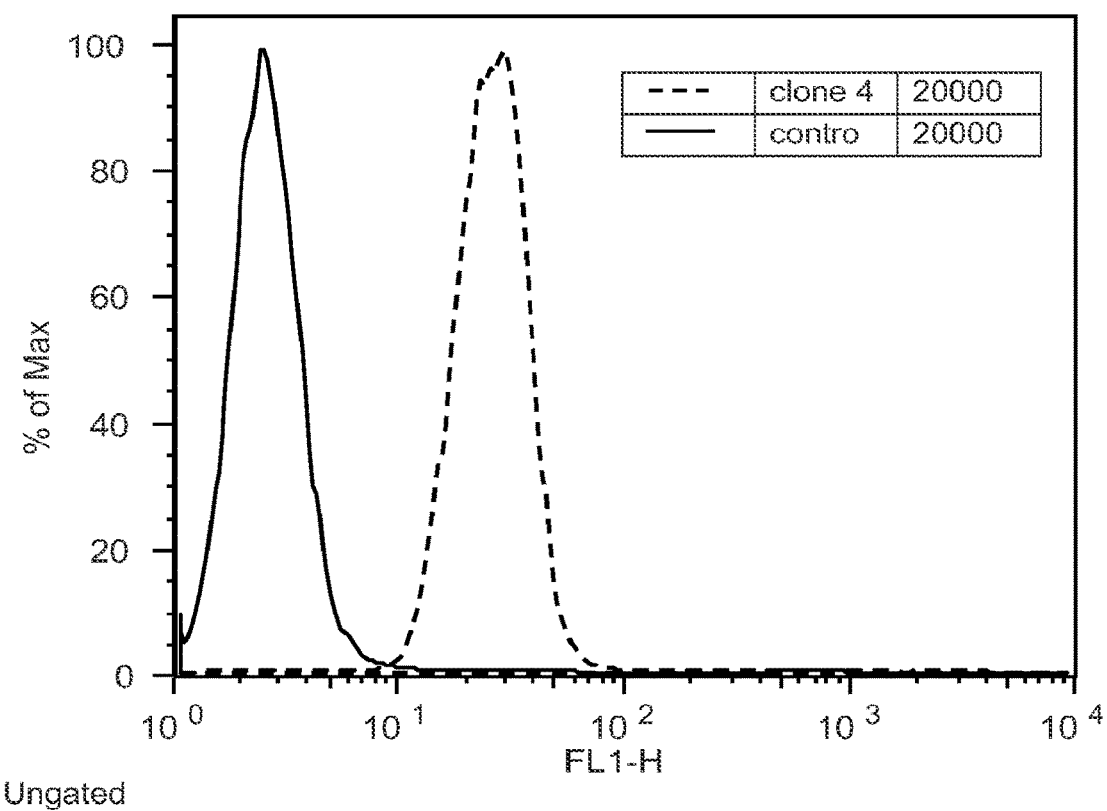
FIG. 6E: clone 4 (dashed line) and control (solid line)
Figure 6F:
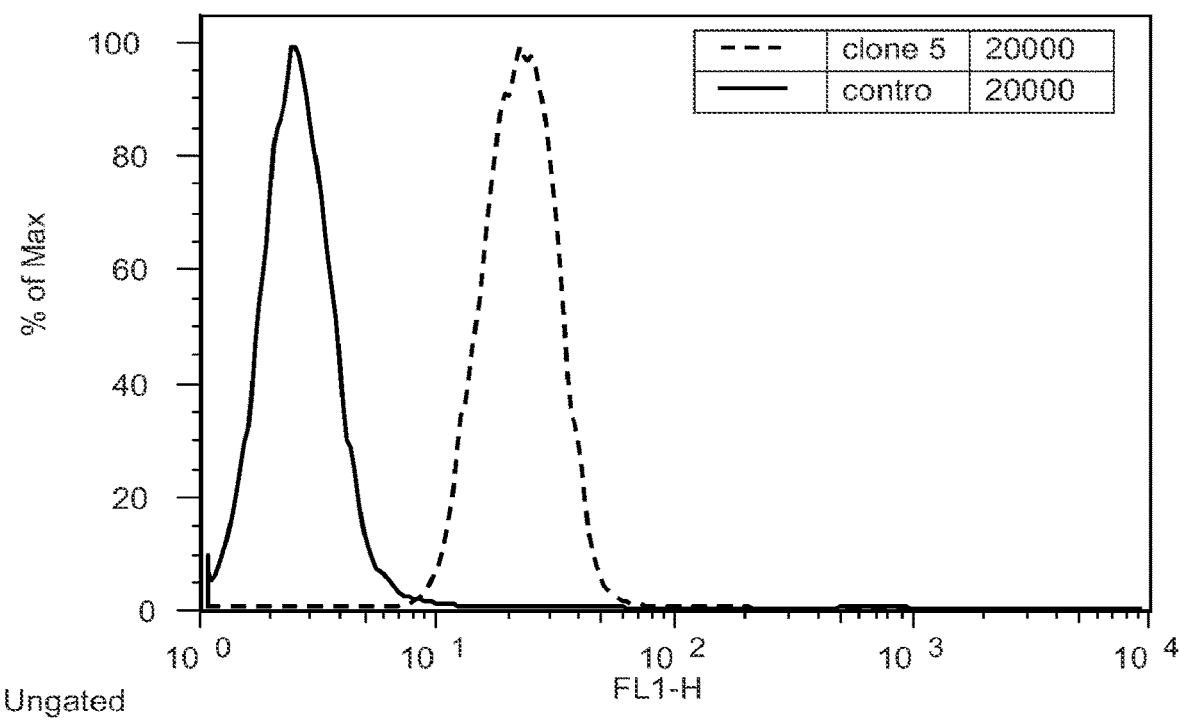
FIG. 6F: clone 5 (dashed line) and control (solid line)
Figure 6G:
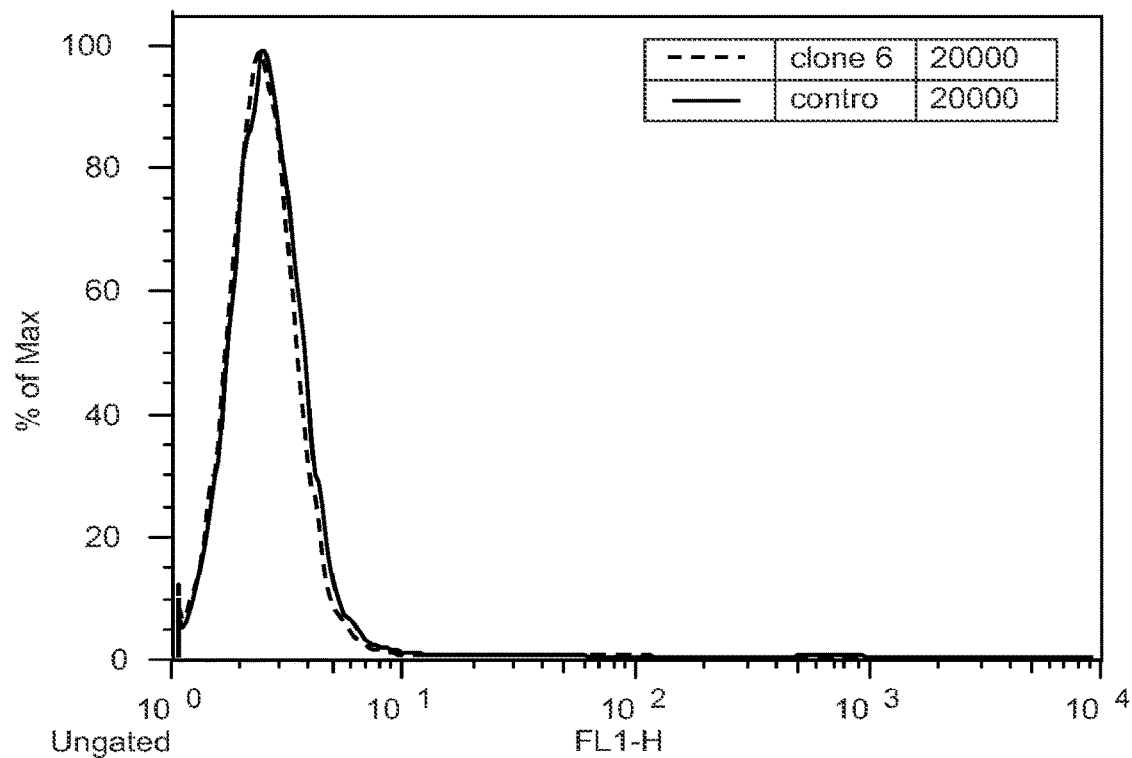
FIG. 6G: clone 6 (dashed line) and control (solid line)
Figure 6H:
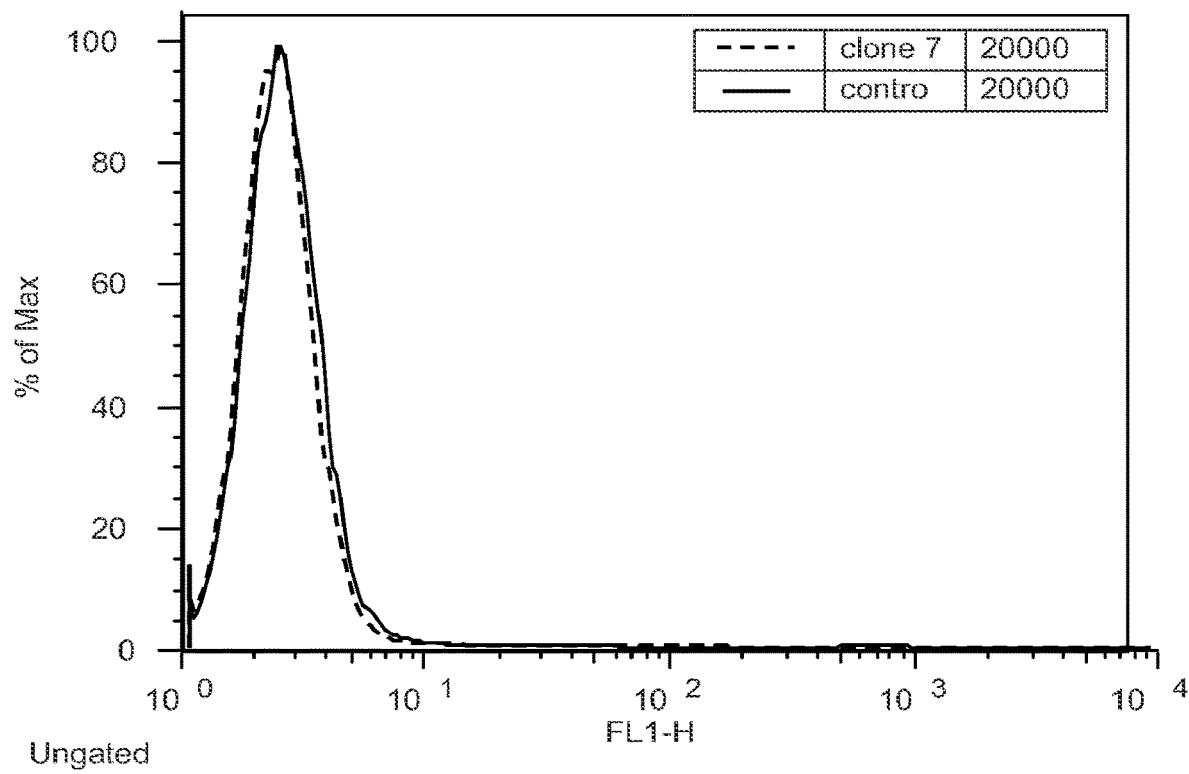
FIG. 6H: clone 7 (dashed line) and control (solid line)
Figure 6I:
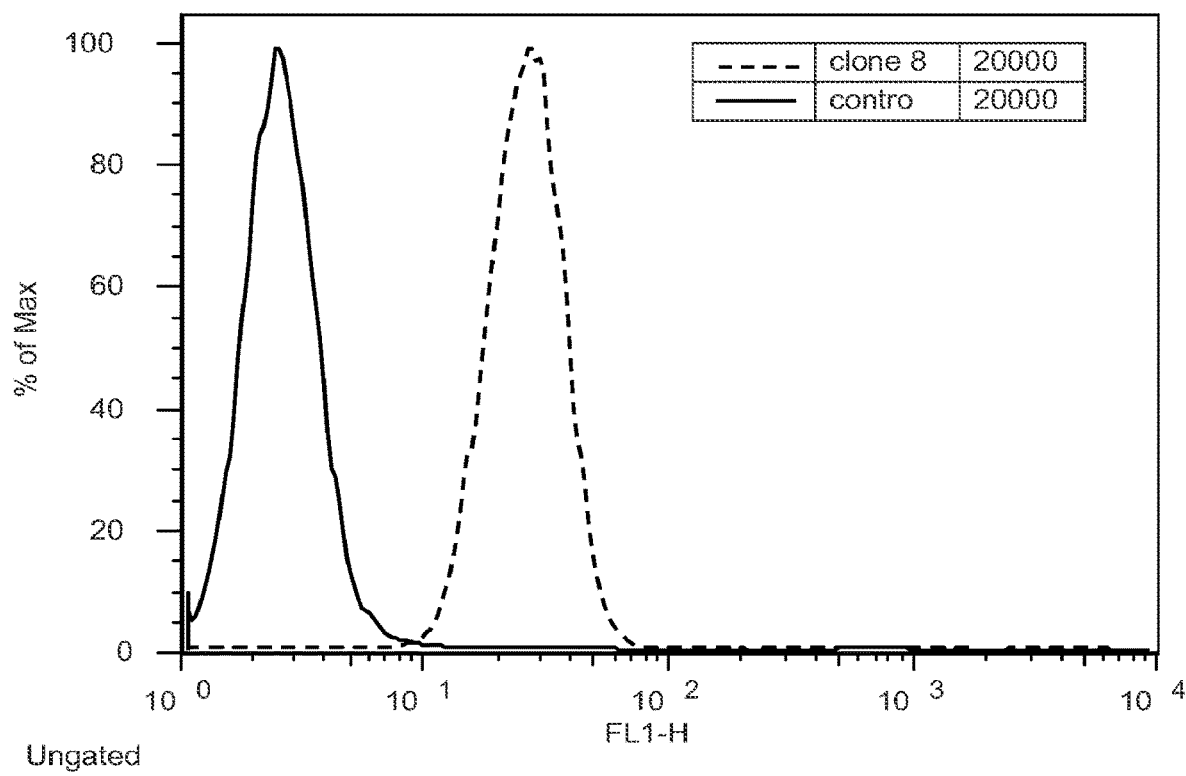
FIG. 6I: clone 8 (dashed line) and control (solid line)
Figure 6J:
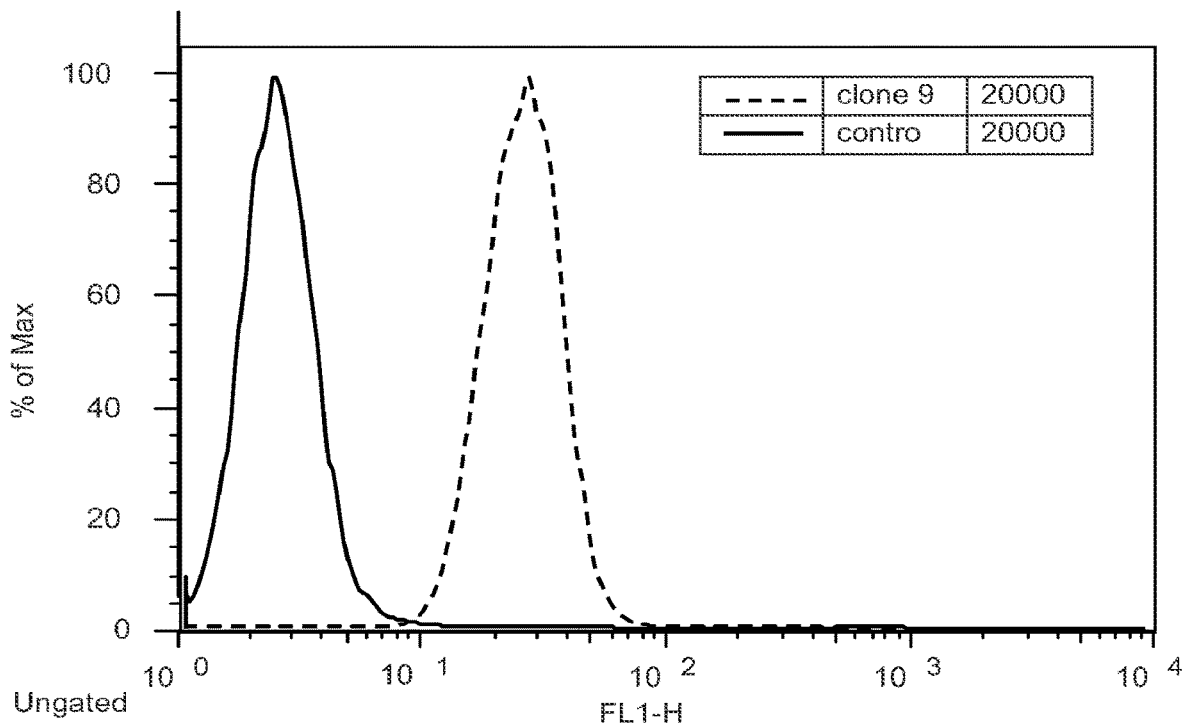
FIG. 6J: clone 9 (dashed line) and control (solid line)
Figure 6K:
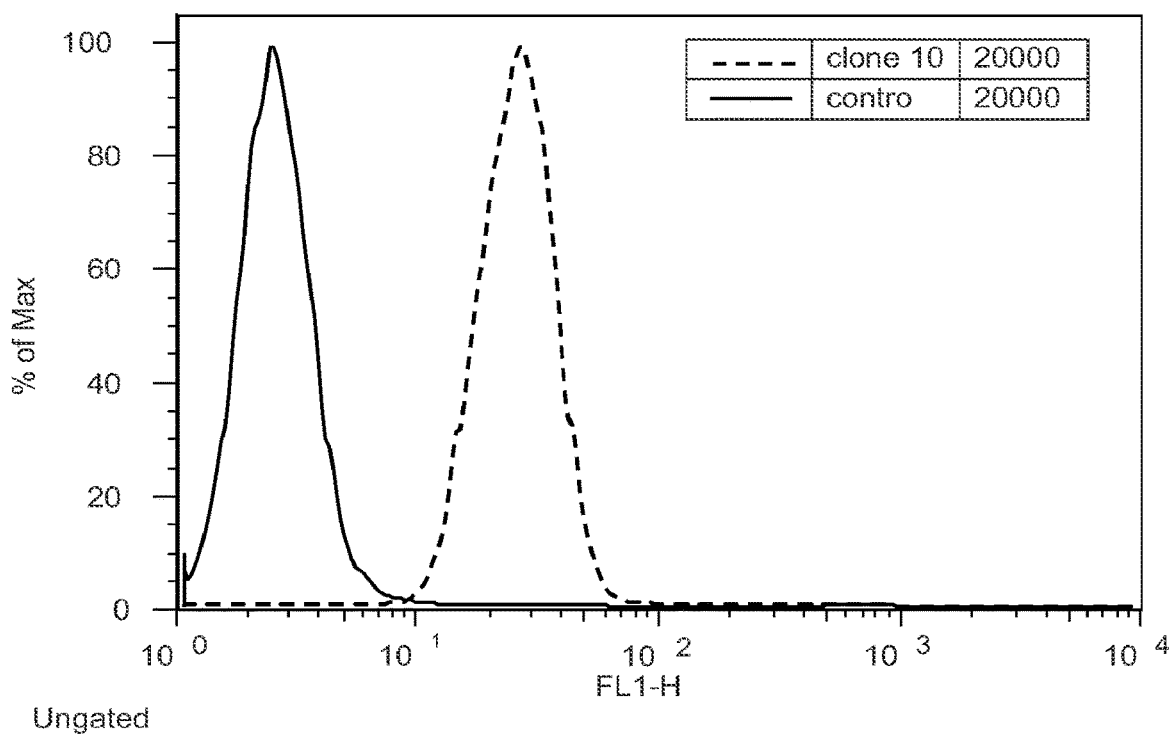
FIG. 6K: clone 10 (dashed line) and control (solid line)
Figure 6L:
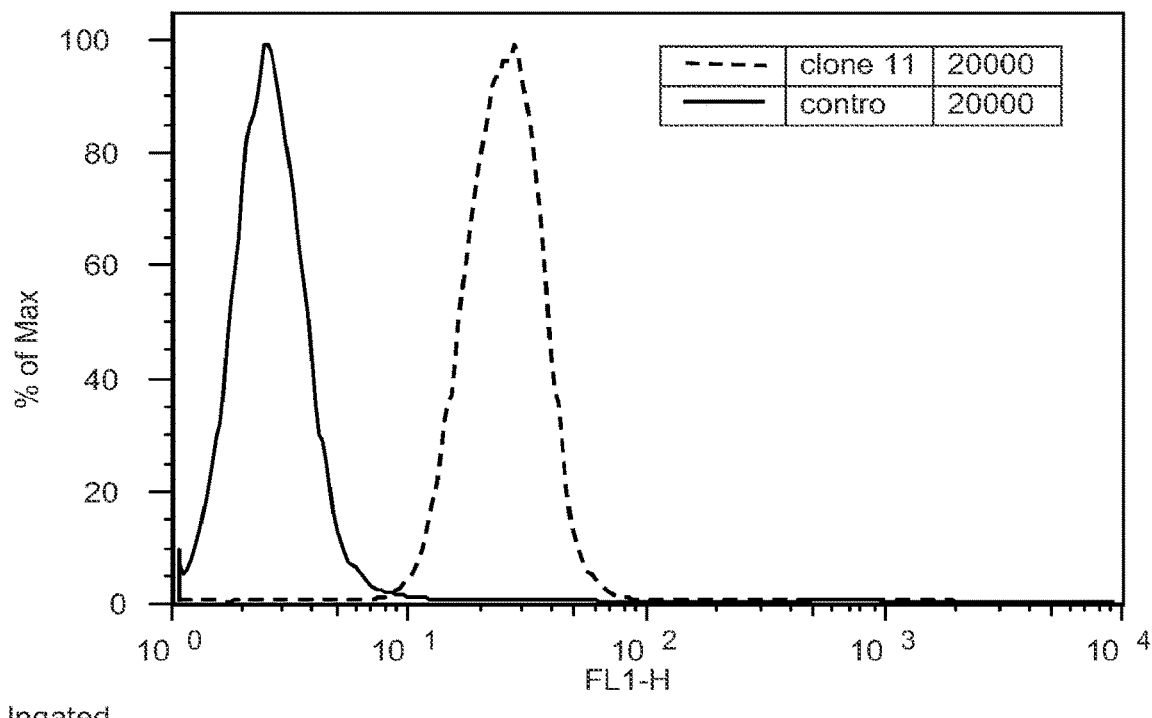
FIG. 6L: clone 11 (dashed line) and control (solid line)
Figure 6M:
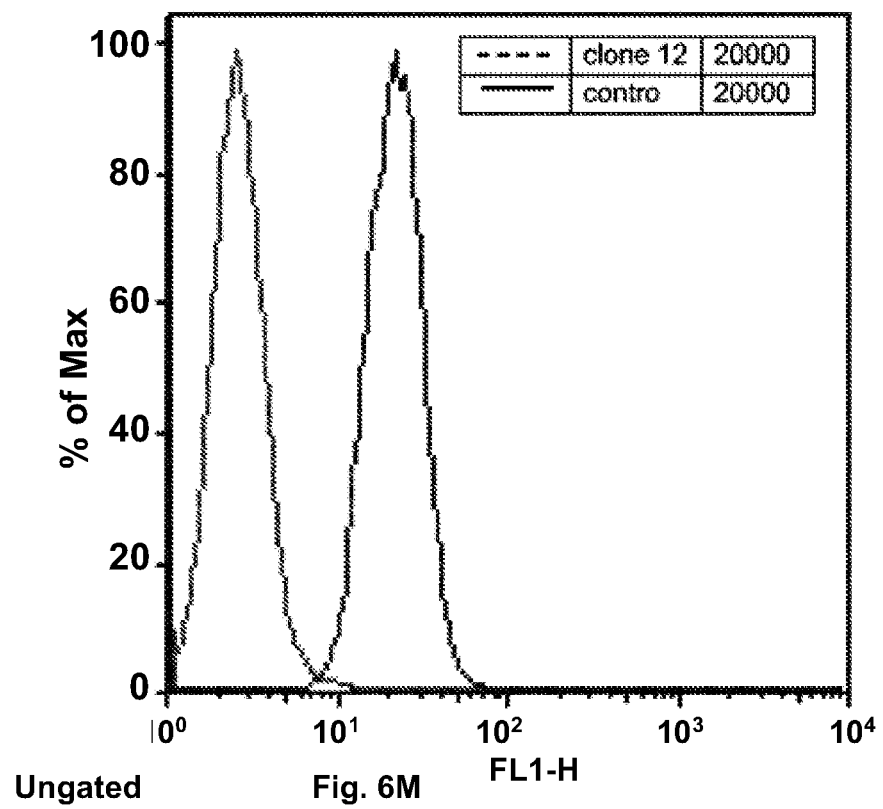
FIG. 6M: clone 12 (dashed line) and control (solid line)
Figure 6N:
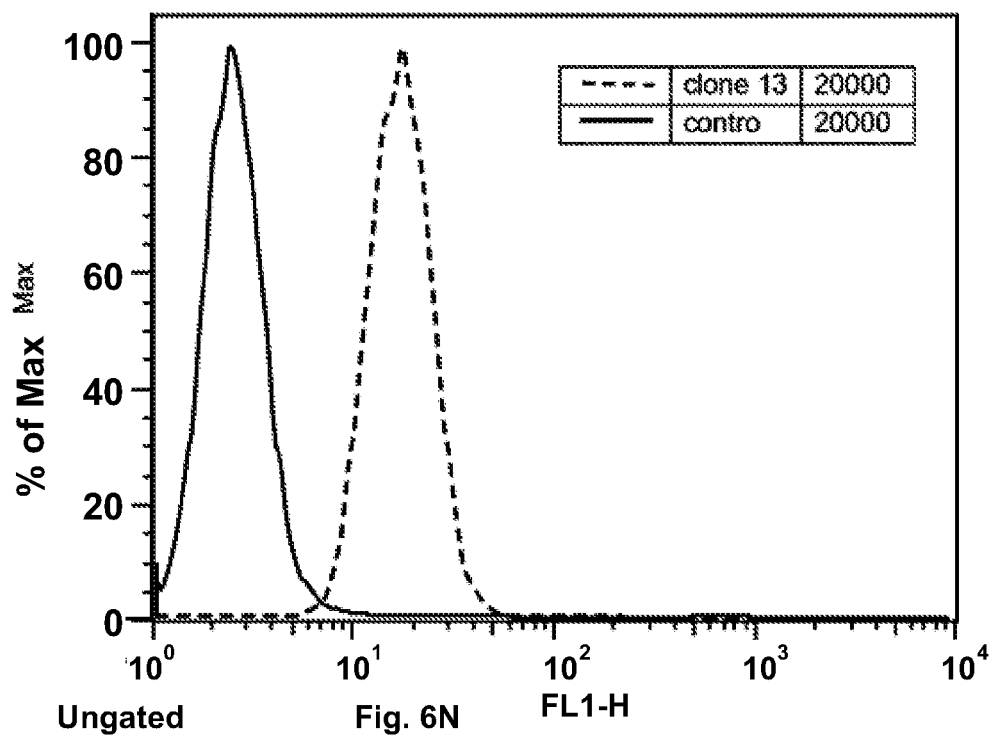
FIG. 6N: clone 13 (dashed line) and control (solid line)
Figure 6O:
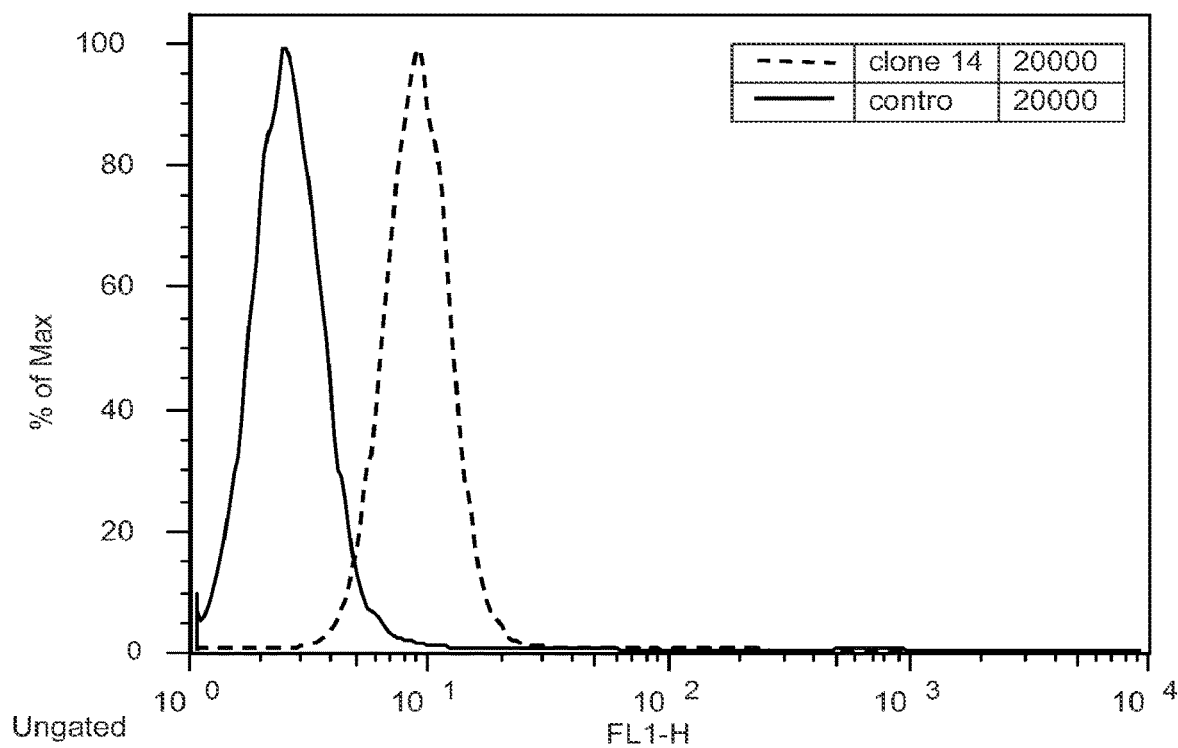
FIG. 6O: clone 14 (dashed line) and control (solid line)
Figure 6P:
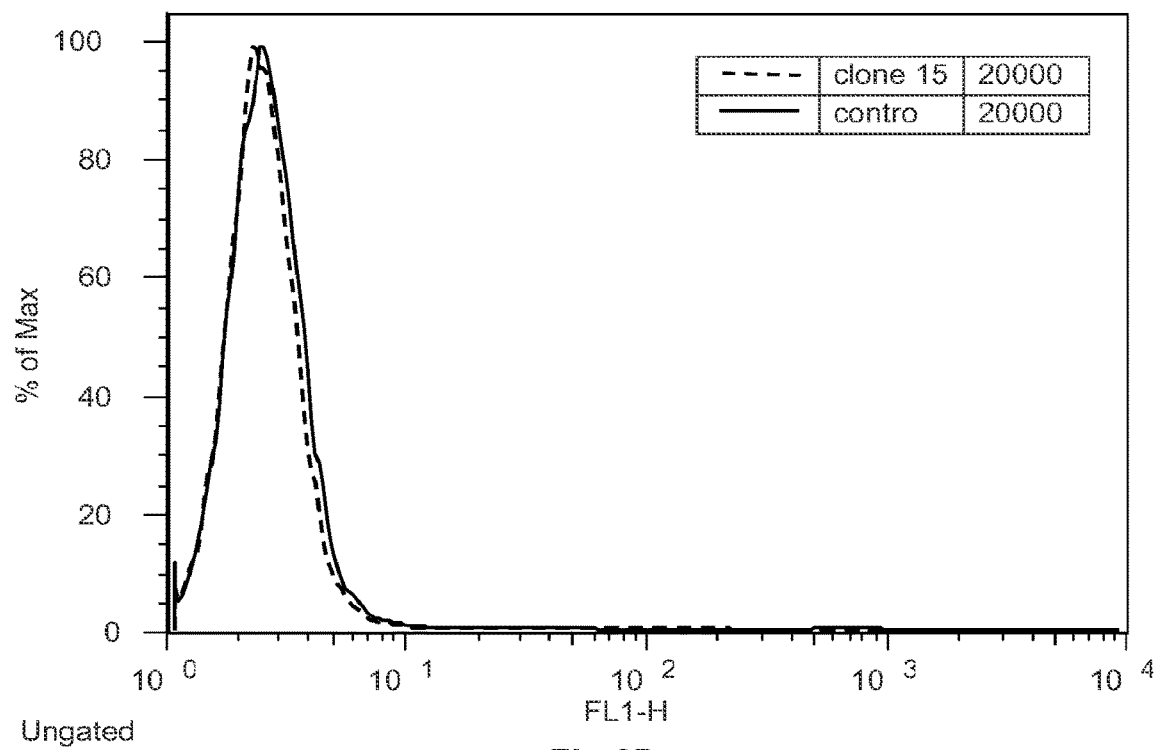
FIG. 6P: clone 15 (dashed line) and control (solid line)
Figure 6Q:
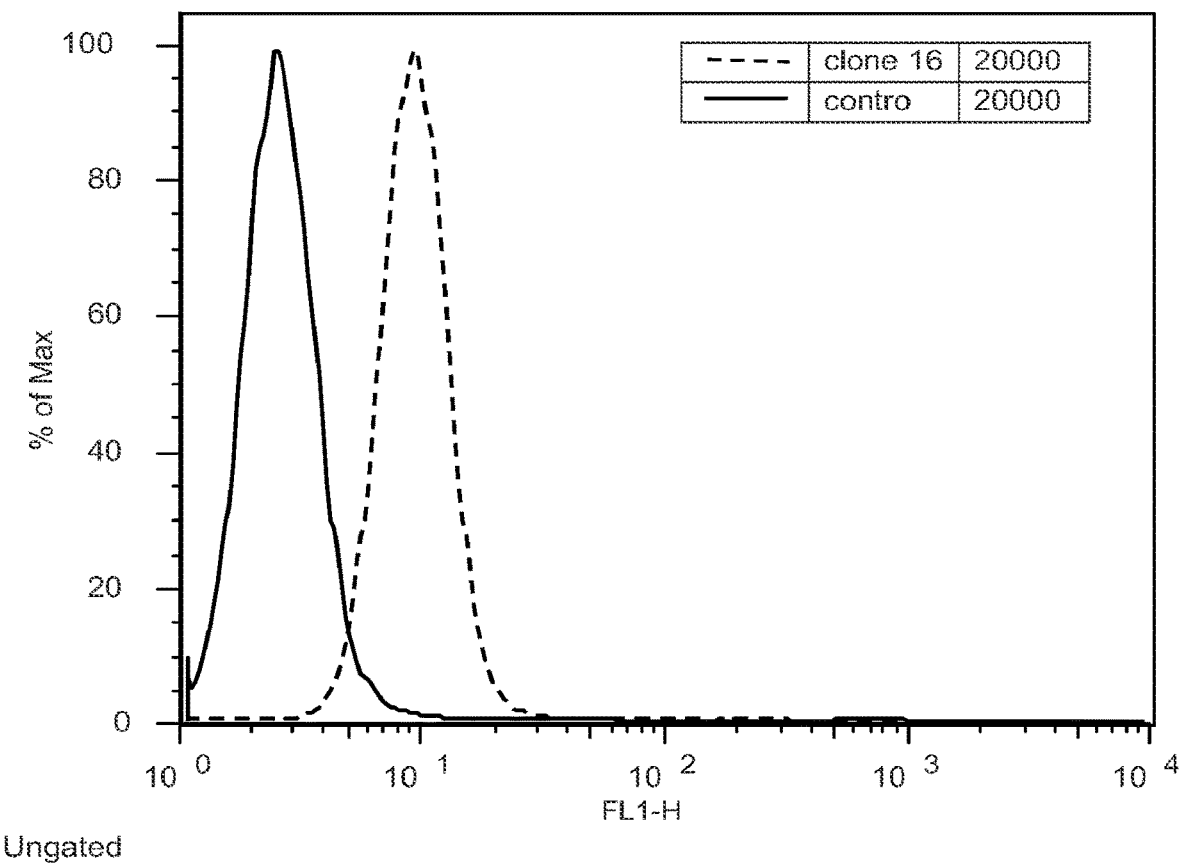

Dual parameter flow cytometry was done in a FACSCalibur instrument (BD Biosciences; Immunocytometry Systems) using an anti-human IgG that reacted with cell bound scFV of the invention (as shown in SEQ. ID. No: 3), but not the cells used in these experiments. CHO cells (which do not express ROR1) and EW36, a human B-cell lymphoma cell line (National Cancer Institute) were stained with culture supernatants of cells transfected to express pCDNA 3.1 (Invitrogen) CH2 CH$_3$ stable scFV (FIGS. 6A-6Q).

In particular, approximately 5×10$^5$ cells were incubated for 20 minutes with the scFV, the cells were then washed and then incubated with an Alexa-488-conjugated goat anti-human-IgG antibody that does not react with EW36 cells in the absence of the cell-bound scFV. Propidium iodide was added to stain dead cells, which could then be excluded from the analysis. Following incubation with the culture supernatants, the cells were washed prior to analysis using a FACSCalibu™ (Becton Dickinson, Mountain View, Calif.). The data analyzed with FlowJo™ software (Tree Star, San Carlos, Calif.). A total of 20,000-gated events were collected for each sample in a list mode file, and data analysis was done using CellQuest™ software (BD Biosciences). The relative log florescence of the cells is depicted on the x-axis. Cells staining with the Alexa-488 conjugated goat antibody are shifted to the right. A histogram of control unstained cells or cells stained with the Alexa-488 conjugated goat antibody in the absence of the scFV are provided for comparison.

The binding activity for. ROR1 expressed on the cell surface membrane was assessed via flow cytometry. The scFV failed to react with CHO cells that do not express ROR1 (FIG. 6A). In contrast, the scFV produced by clones 1, 4-5, 8-14 and 16 reacted with EW36 cells, allowing for detection of the cell-bound scFV using the Alexa-488-conjugated goat antihuman antibody (FIGS. 6B, 6E, 6F, 6I-6O, 6Q, 6R). These data indicate that the single chain scFV of the invention specifically reacts with ROR1 expressed on the surface of viable cells.

Although the invention has been described with reference to the above example, will be understood that modifications and variations are encompassed within the spirit and scope of the invention. Accordingly, the invention is limited only by the following claims.

What is claimed is:

1. A nucleic acid encoding a polypeptide comprising a single-chain variable fragment (scFv) comprising:
   a light chain variable region that comprises a CDR L1 corresponding to amino acid position 27-32 of SEQ ID NO: 2, a CDR L2 corresponding to amino acid position 50-52 of SEQ ID NO: 2, and a CDR L3 corresponding to amino acid position 89-97 of SEQ ID NO: 2; and
   a heavy chain variable region that comprises a CDR H1 corresponding to amino acid position 151-158 of SEQ ID NO: 2, a CDR H2 corresponding to amino acid position 176-182 of SEQ ID NO: 2, and a CDR H3 corresponding to amino acid position 223-233 of SEQ ID NO: 2, wherein said scFv is capable of binding receptor tyrosine kinase-like orphan receptor 1 (ROR1).

2. The nucleic acid of claim 1, wherein said polypeptide is a chimeric antigen receptor.

3. The nucleic acid of claim 1, wherein said scFv is humanized.

4. The nucleic acid of claim 1, wherein said polypeptide is an antibody or antigen binding fragment thereof.

5. The nucleic acid of claim 4, wherein said antibody is humanized.

6. The nucleic acid of claim 1, wherein said polypeptide comprises an Fc region from an antibody.

7. The nucleic acid of claim 6, wherein said Fc region is a human Fc region.

8. The nucleic acid of claim 1, wherein said nucleic acid is a component of an expression vector.

9. The nucleic acid of claim 8, wherein said expression vector is a viral vector.

10. The nucleic acid of claim 9, wherein said viral vector is a lentivirus.

* * * * *

SEQUENCE LISTING

<160> NUMBER OF SEQ ID NOS: 12

<210> SEQ ID NO 1
<211> LENGTH: 269
<212> TYPE: PRT
<213> ORGANISM: Artificial Sequence
<220> FEATURE:
<223> OTHER INFORMATION: Synthetic construct

<400> SEQUENCE: 1

```
Glu Phe Gly Ser Ala Thr Met Gly Trp Ser Cys Ile Ile Leu Phe Leu
1               5                   10                  15

Val Ala Thr Ala Thr Gly Val His Ser Asp Ile Lys Met Thr Gln Ser
            20                  25                  30

Pro Ser Ser Met Tyr Ala Ser Leu Gly Glu Arg Val Thr Ile Thr Cys
        35                  40                  45

Lys Ala Ser Pro Asp Ile Asn Ser Tyr Leu Ser Trp Phe Gln Gln Lys
    50                  55                  60

Pro Gly Lys Ser Pro Lys Thr Leu Ile Tyr Arg Ala Asn Arg Leu Val
65                  70                  75                  80

Asp Gly Val Pro Ser Arg Phe Ser Gly Gly Gly Ser Gly Gln Asp Tyr
                85                  90                  95

Ser Leu Thr Ile Asn Ser Leu Glu Tyr Glu Asp Met Gly Ile Tyr Tyr
            100                 105                 110

Cys Leu Gln Tyr Asp Glu Phe Pro Tyr Thr Phe Gly Gly Gly Thr Lys
        115                 120                 125

Leu Glu Met Lys Gly Ser Thr Ser Gly Ser Gly Lys Pro Gly Ser Gly
    130                 135                 140

Glu Gly Ser Thr Lys Gly Glu Val Lys Leu Val Glu Ser Gly Gly Gly
145                 150                 155                 160

Leu Val Lys Pro Gly Gly Ser Leu Lys Leu Ser Cys Ala Ala Ser Gly
                165                 170                 175

Phe Thr Phe Ser Ser Tyr Ala Met Ser Trp Val Arg Gln Ile Pro Glu
            180                 185                 190

Lys Arg Leu Glu Trp Val Ala Ser Ile Ser Arg Gly Gly Thr Thr Tyr
        195                 200                 205

Tyr Pro Asp Ser Val Lys Gly Arg Phe Thr Ile Ser Arg Asp Asn Val
    210                 215                 220

Arg Asn Ile Leu Tyr Leu Gln Met Ser Ser Leu Arg Ser Glu Asp Thr
225                 230                 235                 240

Ala Met Tyr Tyr Cys Gly Arg Tyr Asp Tyr Asp Gly Tyr Tyr Ala Met
                245                 250                 255

Asp Tyr Trp Gly Gln Gly Thr Ser Val Thr Val Ser Ser
            260                 265
```

<210> SEQ ID NO 2
<211> LENGTH: 244
<212> TYPE: PRT
<213> ORGANISM: Artificial Sequence
<220> FEATURE:
<223> OTHER INFORMATION: Synthetic construct

<400> SEQUENCE: 2

Asp Ile Lys Met Thr Gln Ser Pro Ser Ser Met Tyr Ala Ser Leu Gly
1               5                   10                  15

Glu Arg Val Thr Ile Thr Cys Lys Ala Ser Pro Asp Ile Asn Ser Tyr
            20                  25                  30

Leu Ser Trp Phe Gln Gln Lys Pro Gly Lys Ser Pro Lys Thr Leu Ile
        35                  40                  45

Tyr Arg Ala Asn Arg Leu Val Asp Gly Val Pro Ser Arg Phe Ser Gly
    50                  55                  60

Gly Gly Ser Gly Gln Asp Tyr Ser Leu Thr Ile Asn Ser Leu Glu Tyr
65                  70                  75                  80

Glu Asp Met Gly Ile Tyr Tyr Cys Leu Gln Tyr Asp Glu Phe Pro Tyr
                85                  90                  95

Thr Phe Gly Gly Gly Thr Lys Leu Glu Met Lys Gly Ser Thr Ser Gly
            100                 105                 110

Ser Gly Lys Pro Gly Ser Gly Glu Gly Ser Thr Lys Gly Glu Val Lys
        115                 120                 125

Leu Val Glu Ser Gly Gly Gly Leu Val Lys Pro Gly Gly Ser Leu Lys
    130                 135                 140

Leu Ser Cys Ala Ala Ser Gly Phe Thr Phe Ser Ser Tyr Ala Met Ser
145                 150                 155                 160

Trp Val Arg Gln Ile Pro Glu Lys Arg Leu Glu Trp Val Ala Ser Ile
                165                 170                 175

Ser Arg Gly Gly Thr Thr Tyr Tyr Pro Asp Ser Val Lys Gly Arg Phe
            180                 185                 190

Thr Ile Ser Arg Asp Asn Val Arg Asn Ile Leu Tyr Leu Gln Met Ser
        195                 200                 205

Ser Leu Arg Ser Glu Asp Thr Ala Met Tyr Tyr Cys Gly Arg Tyr Asp
    210                 215                 220

Tyr Asp Gly Tyr Tyr Ala Met Asp Tyr Trp Gly Gln Gly Thr Ser Val
225                 230                 235                 240

Thr Val Ser Ser

<210> SEQ ID NO 3
<211> LENGTH: 807
<212> TYPE: DNA
<213> ORGANISM: Artificial Sequence
<220> FEATURE:
<223> OTHER INFORMATION: Synthetic construct

<400> SEQUENCE: 3
gaattcggat ccgccaccat gggatggtca tgtatcatcc ttttctagt agcaactgca      60 accggtgtac attccgacat caagatgacc cagtctccat cttccatgta tgcatctcta    120
ggagagagag tcactatcac ttgcaaggcg agtccggaca ttaatagcta tttaagctgg    180
ttccagcaga aaccagggaa atctcctaag accctgatct atcgtgcaaa cagattggtt    240 gatgggtcc catcaaggtt cagtggcggt ggatctgggc aagattattc tctcaccatc    300
aacagcctgg agtatgaaga tatgggaatt tattattgtc tacagtatga tgaatttccg    360

```
tacacgttcg gagggggggac caagctggaa atgaaaggct ccacctctgg atccggcaag      420
cccggatctg gcgagggatc caccaagggc gaagtgaaac tggtggagtc tggggggaggc      480 ttagtgaagc ctggagggtc cctgaaactc tcctgtgcag cctctggatt cactttcagt      540
agctatgcca tgtcttgggt tcgccagatt ccagagaaga ggctggagtg ggtcgcatcc      600
attagtcgtg gtggtaccac ctactatcca gacagtgtga agggccgatt caccatctcc      660
agagataatg tcaggaacat cctgtacctg caaatgagca gtctgaggtc tgaggacacg      720
gccatgtatt actgtggaag atatgattac gacgggtact atgcaatgga ctactgggt       780 caaggaacct cagtcaccgt ctcctca                                           807
```

<210> SEQ ID NO 4
<211> LENGTH: 732
<212> TYPE: DNA
<213> ORGANISM: Artificial Sequence
<220> FEATURE:
<223> OTHER INFORMATION: Synthetic construct

<400> SEQUENCE: 4

```
gacatcaaga tgacccagtc tccatcttcc atgtatgcat ctctaggaga gagagtcact       60
atcacttgca aggcgagtcc ggacattaat agctatttaa gctggttcca gcagaaacca      120
gggaaatctc ctaagaccct gatctatcgt gcaaacagat tggttgatgg ggtcccatca      180
aggttcagtg gcggtggatc tgggcaagat tattctctca ccatcaacag cctggagtat      240
gaagatatgg gaatttatta ttgtctacag tatgatgaat ttccgtacac gttcggaggg      300
gggaccaagc tggaaatgaa aggctccacc tctggatccg gcaagcccgg atctggcgag      360
ggatccacca agggcgaagt gaaactggtg gagtctgggg gaggcttagt gaagcctgga      420
gggtccctga aactctcctg tgcagcctct ggattcactt tcagtagcta tgccatgtct      480
tgggttcgcc agattccaga gaagaggctg gagtgggtcg catccattag tcgtggtggt      540
accacctact atccagacag tgtgaagggc cgattcacca tctccagaga taatgtcagg      600
aacatcctgt acctgcaaat gagcagtctg aggtctgagg acacggccat gtattactgt      660
ggaagatatg attacgacgg gtactatgca atggactact ggggtcaagg aacctcagtc      720
accgtctcct ca                                                          732
```

<210> SEQ ID NO 5
<211> LENGTH: 6
<212> TYPE: PRT
<213> ORGANISM: Artificial Sequence
<220> FEATURE:
<223> OTHER INFORMATION: Synthetic construct

<400> SEQUENCE: 5

His His His His His His
1               5

<210> SEQ ID NO 6
<211> LENGTH: 5
<212> TYPE: PRT
<213> ORGANISM: Artificial Sequence
<220> FEATURE:
<223> OTHER INFORMATION: Synthetic construct

<400> SEQUENCE: 6

Gly Gly Gly Gly Ser
1               5

```
<210> SEQ ID NO 7
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 7

Pro Asp Ile Asn Ser Tyr
1               5

<210> SEQ ID NO 8
<211> LENGTH: 3
<212> TYPE: PRT
<213> ORGANISM: Artificial Sequence
<220> FEATURE:
<223> OTHER INFORMATION: Synthetic polypeptide

<400> SEQUENCE: 8

Arg Ala Asn
1

<210> SEQ ID NO 9
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 9

Leu Gln Tyr Asp Glu Phe Pro Tyr Thr
1               5

<210> SEQ ID NO 10
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 10

Gly Phe Thr Phe Ser Ser Tyr Ala
1               5

<210> SEQ ID NO 11
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 11

Ile Ser Arg Gly Gly Thr Thr
1               5

<210> SEQ ID NO 12
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 12

Tyr Asp Tyr Asp Gly Tyr Tyr Ala Met Asp Tyr
1               5                   10
```